US012644084B2

(12) United States Patent
Nurmi et al.

(10) Patent No.: US 12,644,084 B2
(45) Date of Patent: Jun. 2, 2026

(54) APPARATUS AND METHOD FOR CELL CULTIVATION

(71) Applicant: Finnadvance Oy, Oulu (FI)

(72) Inventors: Tuomas Nurmi, Oulu (FI); Nguyen Tuan, Oulu (FI); Prateek Singh, Oulu (FI); Minna Kihlström, Oulu (FI); Jari Moilanen, Oulu (FI)

(73) Assignee: Finnadvance Oy, Oulu (FR)

( * ) Notice: Subject to any disclaimer, the term of this patent is extended or adjusted under 35 U.S.C. 154(b) by 770 days.

(21) Appl. No.: 17/925,181

(22) PCT Filed: May 11, 2021

(86) PCT No.: PCT/FI2021/050351
§ 371 (c)(1),
(2) Date: Nov. 14, 2022

(87) PCT Pub. No.: WO2021/234218
PCT Pub. Date: Nov. 25, 2021

(65) Prior Publication Data
US 2023/0183625 A1     Jun. 15, 2023

(30) Foreign Application Priority Data
May 19, 2020     (FI) ...................................... 20205501

(51) Int. Cl.
*C12M 3/06*          (2006.01)
*C12M 1/12*          (2006.01)
*C12M 1/34*          (2006.01)

(52) U.S. Cl.
CPC ............ *C12M 23/16* (2013.01); *C12M 25/04* (2013.01); *C12M 41/46* (2013.01)

(58) Field of Classification Search
CPC ...... C12M 23/16; C12M 25/04; C12M 41/46; C12M 21/08; C12M 3/00
See application file for complete search history.

(56) References Cited

U.S. PATENT DOCUMENTS

| 2002/0094533 A1 | 7/2002 | Hess et al. |
| 2007/0084706 A1 | 4/2007 | Takayama et al. |

FOREIGN PATENT DOCUMENTS

| WO | 2007106868 A2 | 9/2007 |
| WO | 2015138032 A2 | 9/2015 |

(Continued)

OTHER PUBLICATIONS

Finnish Patent and Registration Office, Search Report, Application No. 20205501, mailed Dec. 15, 2020, 2 pages.

(Continued)

*Primary Examiner* — John Mcguirk
(74) *Attorney, Agent, or Firm* — Ziegler IP Law Group, LLC.

(57) ABSTRACT

An apparatus for cell cultivation includes first reservoir structure, second reservoir structure and a membrane. The first reservoir structure has first matrix of pitted reservoirs and the second reservoir structure has second matrix of pitted reservoirs. The first reservoir structure, second reservoir structure and the membrane are arranged as a stack. The membrane is arranged between first reservoir structure and second reservoir structure, and the first matrix of pitted reservoirs is aligned with the second matrix of pitted reservoirs to couple pitted reservoirs of the first matrix of pitted reservoirs together with pitted reservoirs of the second matrix of pitted reservoirs via the membrane.

10 Claims, 10 Drawing Sheets

(56) References Cited

FOREIGN PATENT DOCUMENTS

| WO | 2016069892 A1 | 5/2016 |
| WO | 2017091718 A1 | 6/2017 |
| WO | 2019033096 A1 | 2/2019 |

OTHER PUBLICATIONS

International Search Report and Written Opinion of the International Searching Authority, European Patent Office, Application No. PCT/FI2021/050351, Aug. 17, 2021, 14 pages.

Zhongyu Li et al. "Assesment of metabolism-dependent drug efficacy and toxicity on a multilayer organs-on-a-chip" Integrative Biology, vol. 8 No. 10, Published on Sep. 7, 2016, DOI: 10.1039/c6ib00162a, www.rsc.org/biology, 9 pages.

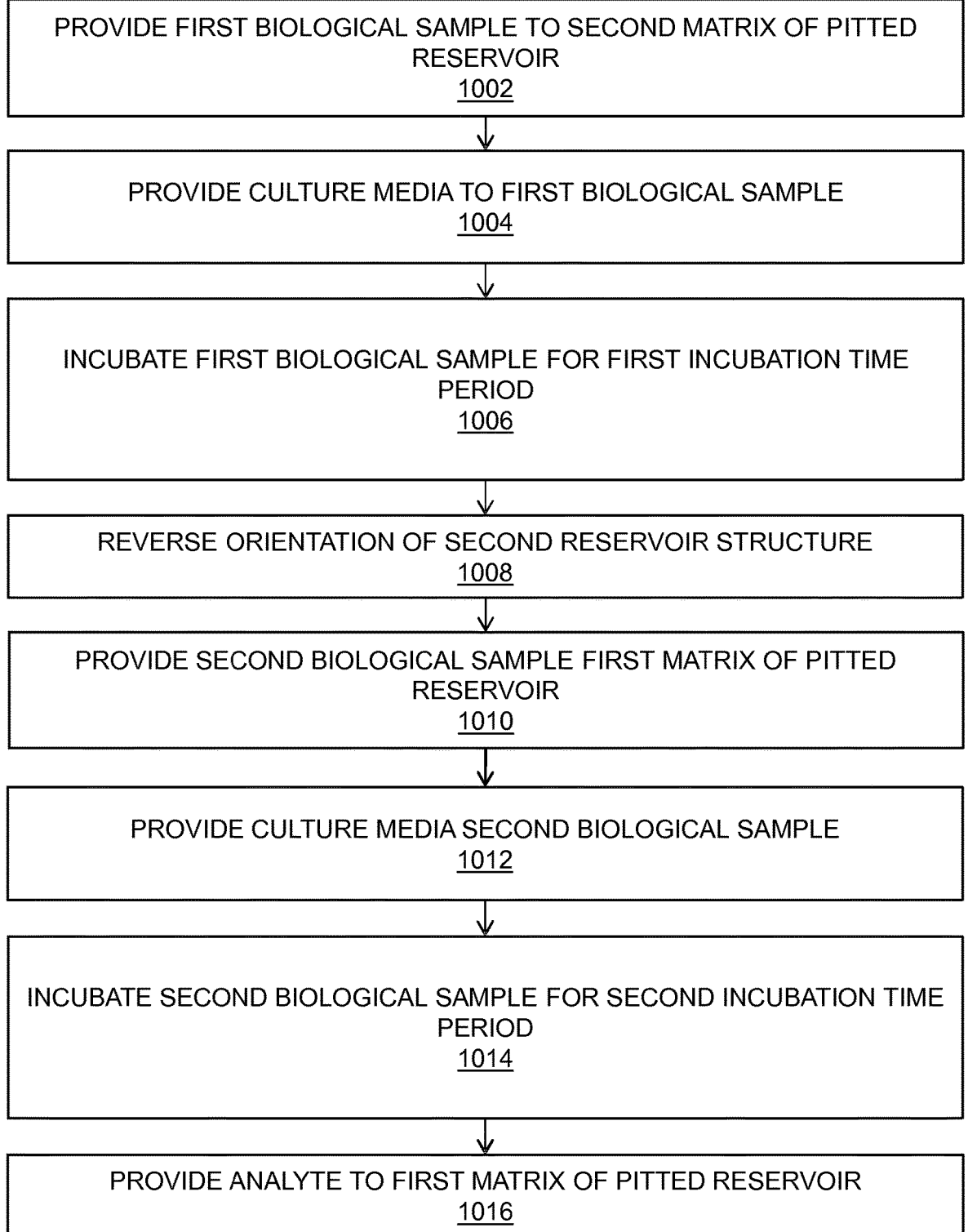

PROVIDE FIRST BIOLOGICAL SAMPLE TO SECOND MATRIX OF PITTED RESERVOIR
1002

PROVIDE CULTURE MEDIA TO FIRST BIOLOGICAL SAMPLE
1004

INCUBATE FIRST BIOLOGICAL SAMPLE FOR FIRST INCUBATION TIME PERIOD
1006

REVERSE ORIENTATION OF SECOND RESERVOIR STRUCTURE
1008

PROVIDE SECOND BIOLOGICAL SAMPLE FIRST MATRIX OF PITTED RESERVOIR
1010

PROVIDE CULTURE MEDIA SECOND BIOLOGICAL SAMPLE
1012

INCUBATE SECOND BIOLOGICAL SAMPLE FOR SECOND INCUBATION TIME PERIOD
1014

PROVIDE ANALYTE TO FIRST MATRIX OF PITTED RESERVOIR
1016

FIG. 10

APPARATUS AND METHOD FOR CELL CULTIVATION

TECHNICAL FIELD

The present disclosure relates generally to cell culture techniques, and more specifically to apparatuses for cell cultivation. Moreover, the present disclosure is concerned with methods of cell cultivation.

BACKGROUND

Cells have an inherent property to grow and differentiate in-vivo. The differentiated cells result in generation of organs that perform desired functions in an organism. However, the cells may also be grown in-vitro to simulate the in-vivo processes associated with an organism. Notably, in-vitro cell culture assays have been an important means for evaluating safety and effectiveness, in other words, efficacy of a chemical compound in preclinical trials.

Conventional methods of pharmacological testing include using in-vitro cell culture assays under optimally balanced conditions. Generally, in-vitro cell culture assays employ monolayer cell culture assays and/or two-dimensional cell culture assays (such as, petri dishes) resulting in monolayer cell cultures. It will be appreciated that growth conditions for cell culture has an impact on the growth and differentiation of cells. Therefore, monolayer cell culture assays or two-dimensional cell culture assays are not able to sufficiently mimic the in-vivo conditions of a cell or cell line as ideally required.

Generally, cell culture assays are extensively used in pharmacological research and testing for humans. Typically, the first trials are performed traditionally on cell lines in a two-dimensional cell culture essay, then on laboratory animals (such as a mice). Those compounds that are deemed to be safe for human trials progress into clinical trials where safety and efficacy are evaluated against current available treatment options and approved drugs. However, in many cases, drugs that produce a positive treatment response to a specific disease or condition in cell culture assays and animals, fail to do so in clinical trials. Such differences in treatment response may predominantly be due to two reasons. Firstly, two-dimensional cell culture assays are not representative of the functional characteristics in living tissues and organs. Secondly, because human bodies function differently in many ways compared to the animal species commonly used for testing drug candidates. Additionally, evaluating a drug in this manner takes on average a period of 10 years and costs vary from hundreds of millions to several billion dollars per approved drug. Furthermore, the occurrence or incidence of many diseases and conditions is so low, that it is uneconomical for drug companies to develop drugs for these conditions.

Recent advances in drug testing have introduced special three-dimensional cell cultivation techniques for pharmacological and toxicological research. The three-dimensional cell cultivation techniques are closer in mimicking the in-vivo conditions of cell as compared to the conventional two-dimensional cell cultures. However, providing growth conditions suitable for keeping the cells alive for a longer period of time, to enable long-term research thereon is still a challenge. Moreover, the conventional three-dimensional cell cultivation techniques do not account for multi-level interactions of different types of cells, the cellular conditions and different concentrations of pharmacological products and/or toxins. Furthermore, the conventional three-dimensional cell cultivation techniques are costly, labour intensive and require periodic changing of cell culture substances done manually. Notably, problems associated with requirement of frequent human intervention have been addressed by providing the three-dimensional cell culture assays with various systems, such as feeding arrangement, harvesting arrangement, and the like. However, despite such systems, the optimum growth of cell cultures remains unsatisfactory, thus rendering the conventional techniques inefficient.

Therefore, considering the foregoing discussion, there exists a need to overcome drawbacks associated with conventional techniques for cell cultivation.

SUMMARY

The present disclosure seeks to provide an apparatus for cell cultivation. The present disclosure also seeks to provide a method of cell cultivation. The present disclosure seeks to provide a solution to the existing problem of in-vitro cell cultivation. An aim of the present disclosure is to provide a solution that overcomes at least partially the problems encountered in prior art, and provides an efficient and reliable design for an apparatus that achieves higher quality of cells defined by an optimal growth of the cells for the purposes of testing potential substances, such as for example drugs, therapeutics, toxins, pollutants, and so forth.

In one aspect, an embodiment of the present disclosure provides an apparatus for cell cultivation, the apparatus comprising a first reservoir structure, the first reservoir structure having a first matrix of pitted reservoirs;

a second reservoir structure, the second reservoir structure having a second matrix of pitted reservoirs; and a membrane, wherein the first reservoir structure, the second reservoir structure and the membrane are arranged as a stack, and wherein the membrane is arranged between the first reservoir structure and the second reservoir structure, and the first matrix of pitted reservoirs is aligned with a second matrix of pitted reservoirs to couple pitted reservoirs of the first matrix of pitted reservoirs together with the pitted reservoirs of the second matrix of pitted reservoirs via the membrane.

In another aspect, an embodiment of the present disclosure provides a method of cell cultivation, the method comprising providing a first biological sample to a base part of two or more pits of a second matrix of pitted reservoirs of a second reservoir structure;

providing a first predefined amount of culture media to the first biological sample;

incubating the provided first biological sample for a first incubation time period to produce a first three-dimensional cell culture at a membrane facing the base part of the two or more pits of the second matrix of pitted reservoir;

reversing an orientation of the second reservoir structure;

providing a second biological sample to a base part of two or more pits of a first matrix of pitted reservoirs of a first reservoir structure, wherein the first reservoir structure is arranged to be opposite to the second reservoir structure;

providing a second predefined amount of culture media via an inlet for the culture media to the second biological sample;

incubating the provided second biological sample for a second incubation time period to produce a second three-dimensional cell culture at the membrane facing the base part of the two or more pits of the first matrix of pitted reservoirs; and providing one or more analytes to the first matrix of pitted reservoirs.

Embodiments of the present disclosure substantially eliminate or at least partially address the aforementioned problems in the prior art and enable effective supply of culture media and a plurality of substances to be tested in different concentrations thereof in the apparatus and enhanced removal and circulation of the used culture media and analytes for optimal growth of cells. Additionally, the embodiments of the present disclosure enable to culture a single cell-type, co-culture two or more cell-types in a high-throughput manner, and analyse different concentrations of one or more pharmacological and/or toxins on such cell-types at the same time, thereby ensuring proper mimic of the in-vivo environment of an organism, however, in a controlled in-vitro environment.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein:

FIG. 10 is an illustration of steps of a method for cell cultivation, in accordance with an embodiment of the present disclosure.

Figure 1:
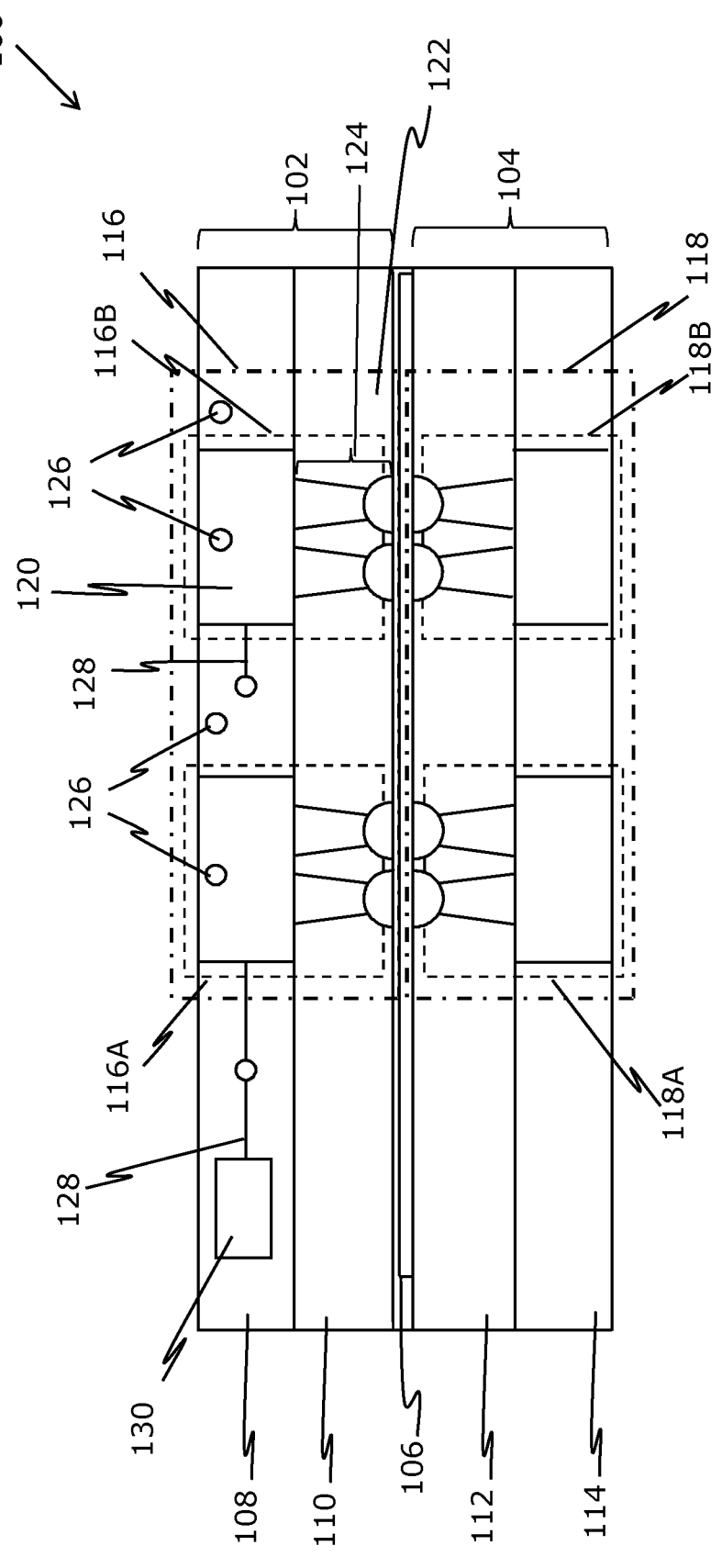
FIGS. 1 and 2 are cross-section of an apparatus for cell cultivation, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides an apparatus for cell cultivation, the apparatus comprising a first reservoir structure, the first reservoir structure having a first matrix of pitted reservoirs;

a second reservoir structure, the second reservoir structure having a second matrix of pitted reservoirs; and a membrane, wherein the first reservoir structure, the second reservoir structure and the membrane are arranged as a stack, and wherein the membrane is arranged between the first reservoir structure and the second reservoir structure, and the first matrix of pitted reservoirs is aligned with a second matrix of pitted reservoirs to couple pitted reservoirs of the first matrix of pitted reservoirs together with the pitted reservoirs of the second matrix of pitted reservoirs via the membrane.

In another aspect, an embodiment of the present disclosure provides a method of cell cultivation, the method comprising providing a first biological sample to a base part of two or more pit of a second matrix of pitted reservoirs of a second reservoir structure;

providing a first predefined amount of culture media to the first biological sample;

incubating the provided first biological sample for a first incubation time period to produce a first three-dimensional cell culture at a membrane facing the base part of the two or more pits of the second matrix of pitted reservoir;

reversing an orientation of the second reservoir structure;

providing a second biological sample to a base part of two or more pits of a first matrix of pitted reservoirs of a first reservoir structure, wherein the first reservoir structure is arranged to be opposite to the second reservoir structure;

providing a second predefined amount of culture media via an inlet for the culture media to the second biological sample;

incubating the provided second biological sample for a second incubation time period to produce a second three-dimensional cell culture at the membrane facing the base part of the two or more pits of the first matrix of pitted reservoirs; and providing one or more analytes to the first matrix of pitted reservoirs.

The present disclosure provides the aforementioned apparatus for cell cultivation. The apparatus of the present disclosure comprises a matrix of volumes for cell culture and a means for supplying a cross-gradient of potential substances for pharmacological and/or toxicological research and testing. The apparatus allows the culturing of a single cell type or co-culture of two or more cell types, such as cell lines, spheroids, organoids, cells embedded in matrix, and so forth until a three-dimensional set of cultured cells is produced in the apparatus. The apparatus of the present disclosure allows analysis and testing of different concentrations of several pharmacological and/or toxicological products on three-dimensional cultured cells. Moreover, the design of the apparatus incorporates flow, vasculature, membranes, barriers and other three-dimensional features of tissues and organs, to replace both the two-dimensional cell culture systems as well as the use of animal models in preclinical drug testing. The design of the apparatus enables efficient consumption of nutrient feed and gases for optimal growth of the cells.

The apparatus is designed to continuously provide fresh cells or biological sample, nutrient feed and products for testing, which further enables optimal growth of cells while maintaining the cells alive in the apparatus. Moreover, the apparatus provides efficient production of cells upon growth, for providing an overall energy, time and cost-efficient apparatus that employs human cells with fluid flow aiming to simulate and mimic fluid flow in human tissues and organs. Furthermore, in order to materialize said apparatus which mimics the natural function of an organ or tissue, eligible fabrication materials known for their microfluidics and flow dynamic properties and suitable for cell culture are employed.

Additionally, beneficially, the apparatus addresses the problem associated with the current organoid and spheroid culture systems with regards to an inability thereof to culture enough organs and spheroids in a satisfactory form factor for high throughput studies. While devices for generating spheroids have become abundant, however, there is a lack of devices and methods for testing drugs and other compounds on these spheroids and organoids in large quantities. In this regard, the apparatus opens avenues for high throughput analysis involving multiple cells culture types and potential analytes and multiple concentrations thereof, in real time.

Throughout the present disclosure, the term "apparatus" refers to a device (namely, a microchip) used for growing an inoculum of cells, isolated from their natural biological environment, i.e. in-vivo, into a mass of cells under controlled conditions, i.e. in-vitro. Said controlled conditions are suitable for an optimal growth of cells and include a suitable container, growth media (comprising nutrient feed, growth factors, hormone), and physicochemical parameters (such as pH, osmotic pressure, humidity, temperature, sterile conditions). Moreover, the apparatus of the present disclosure may be of various shapes (such as round or planar), sizes and fabrication to suit a variety of cell cultures. Furthermore, the apparatus incorporates microfluidic flow, vasculature and barriers to provide living cell-like conditions for the growth of the cells. In this regard, the cells may be derived from microbes, viruses, fungi, plants, animals or humans. It will be appreciated that new cells may be added after a desired growth of cells is achieved. In an example, the apparatus incorporates human cells with fluid flow aiming to simulate and mimic fluid flow in human tissues and organs. Furthermore, the apparatus is suitably configured for physiological structures, tissue parameters, microfluidics, flow dynamics of a natural tissue or organ in natural conditions.

Beneficially, such organ-on-chip devices may be used to analyse effects of various pharmacological or toxicological compounds on the human cells.

In the present disclosure, the apparatus is used for cell cultivation. The term "cell cultivation" refers to a process of growing cells, having a growth rate, from a small number to a larger number in an artificially created environment under controlled conditions. Moreover, the small number of cells are provided as input for the apparatus and large number of cells is received as output. Optionally, the cell cultivation is a three-dimensional cell cultivation. The term "three-dimensional cell cultivation" as used herein refers to cultivation of single or multiple cells under controlled conditions to grow and interact with the surroundings thereof in three dimensions similar to the in-vivo cell growth. The three-dimensional cell cultivation uses an acellular three-dimensional scaffold (or substrate) or a scaffold-free liquid suspension media for growing cells. The three-dimensional substrate includes, but is not limited to, hydrogel matrix, porous membranes and solid scaffolds. Beneficially, the three-dimensional cell cultivation provides three-dimensional cell cultures with more contact space for cell adhesion and intracellular signalling. Beneficially, the three-dimensional cell cultures may be used in drug discovery, tissue engineering and pharmacological and toxicological research, for example, analysing effect of various substances on the cells.

Optionally, the apparatus is manufactured using a fabrication material selected from any of: polydimethylsiloxane (PDMS), Flexdym™ polymer, thiol-ene polymer, UV-curable epoxy resin-based photoresist, PMMA, polystyrene, PLGA, soft thermoplastic elastomer (sTPE), styrenic block copolymer (BCP), SU-8 polymer, or any combination thereof. Notably, the apparatus is manufactured from a fabrication material that is typically waterproof and strong enough to withstand effects of various biological and/or biochemical processes during use. Said fabrication material of the apparatus is suitable for cell culture and enabling efficient growth of the biological sample. In an example, the fabrication material of the apparatus allows consistent exchange of gas molecules or small molecules between two liquids or a liquid and a gas therethrough without direct contact. Such indirect diffusion of molecules keeps the cells fresh and alive for a longer period. The apparatus is manufactured using multiple layers of fabrication material. Typically, the multiple layers of said fabrication material has an adequate thickness to hold a weight of the growing cells and carry out various processes. In an example, the apparatus holding a large weight of the biological sample may thereby require larger thickness. Moreover, each layer of said fabrication material provides for injection of fluids for research and analysis. Optionally, said fabrication material provides an optimum flow rate, microfluidics, physiological conditions and so forth thereby mimicking the natural function of a biological sample.

Optionally, manufacturing and processing techniques may include, but not limit to, injection moulding, over moulding, three-dimensional printing, photolithography, and so on. In an example, polydimethylsiloxane (PDMS), a mineral-organic polymer containing carbon and silicon, is used as the fabrication material for the manufacture of the apparatus, PDMS is known for its biocompatibility, transparency, flexibility, gas permeability, low solubility and low surface tension. In this example, manufacturing the apparatus includes mixing the PDMS base monomer with a cross-linking agent (for curing of PDMS), pouring the resulting mixture into a micro-structured mould of desired shape and size, and subjecting thereof to an optimum temperature to obtain an elastomeric replica of the mould. Moreover, multiple layers of PDMS are stacked on top of each other to result in a structure with complex geometry enabling addition of membranes, barriers, conduits, and other such potential things that may be integrated as desired. For example, the apparatus may comprise 6 layers of PDMS, each with a thickness in a range between 100-3000 micrometre (μm). The thickness of each layer of the apparatus can be for example from 100, 500, 1000, 1500, 2000 or 2500 μm up to 500, 1000, 1500, 2000, 2500 or 3000 μm. It will be appreciated that the layers of the apparatus containing the matrix of pitted reservoir will have additional thickness further corresponding to the height of the matrix of pitted reservoirs. In this regard, the overall thickness of the layer comprising the matrix of pitted reservoir may be in a range between 2-10 millimetre (mm). The overall thickness of the layer comprising the matrix of pitted reservoir can be for example from 2, 3, 4, 5, 6, 7, 8 or 9 mm up to 3, 4, 5, 6, 7, 8, 9 or 10 mm.

Optionally, the apparatus may be designed as a clear plate or chip for improved optical clarity or as coated plate or chip for use in fluorescence and/or luminescence studies. Beneficially, the apparatus may be used to fit with a variety of standard multi-well cell culture plates for various applications ranging from cloning, incubations, and so forth. Typically, the standard multi-well cell culture plates have defined outer dimensions, generally in a 2:3 rectangular matrix. The standard multi-well cell culture plate may be selected from, for example, the standard 6, 12, 24, 48, 96, 384, 1536 and 3456-well cell culture plate comprising a 2×3, 3×4, 4×6, 6×8, 8×12, 16×24, 32×48 and 48×72 matrix of wells for high throughput analysis. As a result, the well dimensions, diameter and distances between the wells of the multi-well cell culture plates is also defined as per the industry standards. Optionally, the apparatus of the present disclosure can be produced in large quantities in sheets and punched into a desired shape, such as spheres, to fit the wells of the multi-well cell culture plates. It will be appreciated that the dimensions and volumes enclosed thereby cannot be larger than the well itself. Moreover, the apparatus should have same outer dimensions as per its use with the different multi-well cell culture plates formats. Optionally, a length of the apparatus ranges between 6 to 300 millimetres (mm), a width of the apparatus ranges between 6 to 200 mm, and a height of the apparatus ranges between 5 to 10 mm. The length of the apparatus can be for example from 6, 10, 20, 30, 40, 50, 100, 150, 200 or 250 mm up to 20, 30, 40, 50, 100, 150, 200, 250 or 300 mm, the width of the apparatus can be for example from 6, 10, 20, 30, 40, 50, 100 or 150 mm up to 20, 30, 40, 50, 100, 150 or 200 mm, and the height of the apparatus can be for example from 5, 6, 7, 8 or 9 mm up to 6, 7, 8, 9 or 10 mm. In an example, a smallest possible first matrix of pitted reservoir of 2×2 array unit has a length and width as 12 mm×12 mm with wells of height 6 mm, wherein a well of the first matrix of pitted reservoir contains four pits.

The apparatus for cell cultivation comprises the first reservoir structure, the first reservoir structure having a first matrix of pitted reservoirs and the second reservoir structure, the second reservoir structure having a second matrix of pitted reservoirs. The first reservoir structure and the second reservoir structure resemble wells for cultivating various types of biological samples. The first reservoir structure has a first surface and a second surface opposite the first surface. The first reservoir structure has a first opening on the first surface and a second opening on the second surface, wherein the first opening faces the top surface of the apparatus. The first reservoir structure encloses a first volume between the first and second openings. The first volume encloses the first matrix of pitted reservoirs. The first matrix of pitted reservoirs being embedded in the first reservoir structure. Similarly, the second reservoir structure has a third surface and a fourth surface opposite the third surface. The second reservoir structure has a third opening on the third surface and a fourth opening on the fourth surface, wherein the fourth opening faces the bottom surface of the apparatus. The second reservoir structure encloses a second volume between the third and fourth openings. The second volume encloses the second matrix of pitted reservoirs. The second matrix of pitted reservoirs being embedded in the second reservoir structure.

Optionally, the diameter of the first and second pitted reservoirs may typically range from, for example, 6.35, 6.40, 6.45, 6.50, 6.55, 6.60, 6.65, 6.70, 6.75 or 6.80 millimetre (mm) up to 6.40, 6.45, 6.50, 6.55, 6.60, 6.65, 6.70, 6.75, 6.80 or 6.85 mm. Beneficially, said diameter of the pitted reservoirs is ideal to fit snugly inside a standard well of a multi-well cell culture plates, preferably a 96-well cell culture plate, or it may be such that it is clearly smaller than the standard well of the multi-well cell culture plates.

Throughout the present disclosure, the term "matrix of pitted reservoirs" as used herein refers to an arrangement of one or more pitted reservoirs in the first reservoir structure and the second reservoir structure. The pitted reservoirs are arranged in rows which can be arranged in an array unit. Optionally, the array unit may be selected from a square array unit or a hexagonal array unit. More optionally, the square array unit comprises four or more pitted reservoir in a matrix of pitted reservoir, while a hexagonal array comprises six or more pitted reservoir in a matrix of pitted reservoir. Optionally, the square array unit may have one of: a 2×2 matrix comprising 4 pitted reservoirs, a 3×3 matrix comprising 9 pitted reservoirs, a 4×4 matrix comprising 16 pitted reservoirs, a 5×5 matrix comprising 25 pitted reservoirs, a 10×10 matrix comprising 100 pitted reservoirs, and so forth.

Moreover, each of the pitted reservoirs has a wall enclosing a predefined volume of liquid media and biological sample. Moreover, said wall enables the liquid media, including the culture media and the one or more analytes, to be available for the growth of the biological sample and further analysis thereon. Optionally, the wall of the pitted reservoir has a height ranging between 1 to 10 millimetre and a thickness ranging between 0.5 to 3.0 millimetre. For example, the height of the wall may typically be from 1, 2, 3, 4, 5, 6, 7, 8 or 9 millimetre (mm) up to 2, 3, 4, 5, 6, 7, 8, 9 or 10 mm, and the thickness of the wall may typically be from 0.5, 1.0, 1.5, 2.0 or 2.5 mm up to 1.0, 1.5, 2.0, 2.5 or 3.0 mm. Optionally, the thickness of the wall is half the distance between two adjacent pitted reservoirs embedded in the first reservoir structure.

Optionally, the one or more pitted reservoirs of the first reservoir structure and the one or more pitted reservoirs of the second reservoir structure may be arranged in array units similar to or different from each other in size, shape, number and orientation. For example, the matrix of pitted reservoirs of the first reservoir structure is a square array unit of 3×3 matrix comprising 9 pitted reservoirs having cylindrical cross-section, whereas the matrix of pitted reservoirs of the second reservoir structure is a hexagonal array unit comprising 7 pitted reservoirs having cylindrical or conical cross-section.

The apparatus for cell cultivation comprises the membrane. The membrane is a planar sheet having a first face and a second face. Specifically, the membrane is composed of a material that is biocompatible and selectively permeable. A selectively permeable membrane, such as for example a semi-permeable membrane, has a plurality of pores therein to enable gases or liquids (such as microfluid) to pass therethrough.

Optionally, the membrane is a porous membrane with pore size ranging between 5 to 30 micrometres. Optionally, the membrane is of varying pore size and shape. For example, typically the pore size of the membrane may be from 5, 10, 15, 20 or 25 micrometres (µm) up to 10, 15, 20, 25 or 30 µm. Optionally, the shape of the pore may be of a circular cross-section, an elliptical cross-section, a polygonal cross-section, and so forth.

Moreover, the first reservoir structure, the second reservoir structure and the membrane are arranged as a stack. The membrane is arranged between the first reservoir structure and the second reservoir structure. Furthermore, the first matrix of pitted reservoirs is aligned with a second matrix of pitted reservoirs to couple pitted reservoirs of the first matrix of pitted reservoirs together with the pitted reservoirs of the second matrix of pitted reservoirs via the membrane. The first reservoir structure and the second reservoir structure are arranged opposite to each other on the either sides, i.e. the first face and the second face of the membrane. In this regard, the membrane is arranged between the first reservoir structure and the second reservoir structure such that the second surface of the first reservoir structure is facing the first face of the membrane and the third surface of the second reservoir structure is facing the second face of the membrane. Moreover, the first matrix of pitted reservoirs is aligned with the second matrix of pitted reservoirs to couple a volume enclosed by the first matrix of pitted reservoirs and a volume enclosed by the second matrix of pitted reservoirs via the membrane. It will be appreciated that the presence of semi-permeable membrane between the oppositely aligned first and second reservoir structures enables supply of a liquid media from the first reservoir structure to the second reservoir structure through the membrane.

Further benefit of the apparatus with a structure in which, two or more pits of the first matrix of pitted reservoirs are arranged to be coupled together with respective two or more pits of the second matrix of pitted reservoirs, via a membrane, is to enable the cultivation of larger three dimensional cell structures in comparison to having only one matrix of pitted reservoirs. Also the provided structure enables growing cells of a first type in the first matrix and cells of a second type in the second matrix. As an example, when using the apparatus for analysing an organoid which comprises two different spheroids, namely a first type of spheroid and a second type of spheroid. In such a case the first type of spheroid can be cultivated in the pits of the first matrix and the second type of spheroid can be cultivated in the pits of the second matrix. The first type of spheroid and the second type of spheroid are thus coupled via membrane to form the organoid. This way of forming the organoid can be done in a controlled manner.

Yet another benefit (another example), when using the apparatus for analysing an organoid, which comprises a spheroid and one or more types of cells. In such a case the spheroid can be cultivated in the pits of the first matrix and the one or more types of cells can be cultivated in the pits of the second matrix. In the case of a plurality of cell types they can be applied in a series so as to create a series of cell layers of different types. The spheroid and the one or more types of cells are thus coupled via membrane to form the organoid. This way of forming the organoid can be done in a controlled manner.

It will be appreciated that in order to achieve cell cultivation in a high throughput manner, the number of pits in each pitted reservoir is as high as possible. In such case, the size of each of the number of pits in the pitted reservoir may be reduced, for example the thickness of pits, to increase the number of pits per square area of the pitted reservoir. However, increasing the number of pits with reduced size may result in lower quality apparatus and ineffective cell cultivation. In an example, the higher number of pits may risk material integrity of the apparatus at the time of moulding and demoulding, and inaccurate placement of apparatus in standard multi-well cell culture plates, such as for example a misoriented placement leading in misloading of the biological sample to a corner of the bottom of the pit and not the centre of the pit. In this regard, the apparatus of the present disclosure provides each of the pitted reservoir having for example 4 to 25 pits therein to generate a high-throughput cell cultivation without risking the material integrity of the apparatus.

In an embodiment, one or more of the pitted reservoirs, comprises a common volume and a pit volume, wherein the pit volume comprises of two or more pits. In one example the pit volume can comprise one or more pits. Notably, the apparatus is manufactured from multiple layers of fabrication material, covering an area of the apparatus, with various structures, such as pitted reservoirs, integrated therein. Each of the two or more pits enclose a volume, referred to as the "pit volume". The upper layers of the one or more pitted reservoir enclose a volume different from the pit volume, referred to as the "common volume". In other words, the volume of the one or more pitted reservoir is a sum of said common volume and said pit volume, wherein a base of the common volume is adjacent to a top of the pit volume. Specifically, the common volume, when in use, contains the culture media and one or more analytes supplied to the one or more pitter reservoirs, and the pit volume, when in use, contains the biological sample and a predefined amount of culture media and one or more analytes. Throughout the present disclosure, the term "pits" refer to miniaturised wells for enabling cell cultivation therein, which is discussed later in the present disclosure. The two or more pits have a volume for holding a biological sample and a predefined amount of culture media for growth thereof.

Optionally, each of the two or more pits comprises a feeder part, connected to the common volume via a first end of the feeder part, and a base part, connected to a second end of the feeder part via a first end of the base part, and the base part having an opening at a second end of the base part facing the membrane and the base part is configured to accommodate a biological sample for cell cultivation when in use. The feeder part and the base part refers to the upper part and bottom part of the pit, respectively. The feeder part has a side wall at an angle with respect to the base of the common volume. The feeder part receives the biological sample and the culture media from the first end thereof. The pit receives the culture media from the common volume. The biological sample and the culture media are provided from the feeder part to the second end of the base part where the biological sample is allowed to grow. As a result, the feeder part and the base part filled with the culture media couple together the common volume and the pit volume. Moreover, the biological sample is loaded at the second end of the base part, wherein the second end of the base part is open and faces the membrane at one of the first or second face thereof. As a result, the biological sample is grown on the first or second face of the membrane facing the base part of the two or more pits.

Optionally, the common volume comprises one or more openings for a microfluid channel. The term "microfluid channel" as used herein refers to a capillary arrangement for supplying a fluid (such as the liquid media) to the apparatus. Optionally, the microfluid channel is integrated into the apparatus, i.e. in between the PDMS layers. The microfluid channel supplies the culture media and one or more analytes to the first reservoir structure, when in operation. Moreover, the microfluid channel is configured to supply different concentrations of the one or more analytes to each of the pitted reservoirs of the first matrix of pitted reservoirs of the first reservoir structure. Furthermore, the microfluid channel is configured to provide different flow rates of the one or more analytes in corresponding pitted reservoirs. Notably, the different flow rate of the culture media and one or more analytes flowing through said microfluid channel corresponds to a fabrication material of the microfluid channel, a thickness of the fabrication material of the microfluid channel, a viscosity of the culture media and one or more analyte, concentrations of the one or more analytes, and so forth. Optionally, the microfluid channels may be manufactured using the same fabrication material as that of the layers of the apparatus or using a different material, for example Teflon, glass, fibre optic, and so forth. More optionally, the multiple layers of the fabrication material of the apparatus, with microfluid channels integrated therein, are tightly sealed (or adhered to each other) to prevent fluid flowing through the microchannel from flowing out of the microfluid channel. Optionally, the one or more analytes may include, but do not limit to, therapeutics, drugs, pollutants and toxins.

According to an embodiment pitted reservoirs comprise a common volume and a pit volume, wherein the pit volume comprises two or more pits. The two or more pit volumes have a feeder part and base part and the common volume comprises one or more openings for a microfluid channel. Technical effect of this is that the common volume and the microfluid channels enables to provide a culture media for each of the two or more pit volumes in a controlled manner. Indeed this configuration in which a common volume have two more pits, such as 2, 5, 10, 20, 50, 100 pits, enables to run statistically relevant experiments. Since of the pit volumes comprise two or more pits each of the two or more pits (of each volume) can be thus provided with same culture media with same concentrations and flows. This enables to make statistically relevant experiments, since microfluid channels can be configured to provide different culture media concentrations and different flow rates to each different volumes. This way each pit of each different volumes receives same amount of culture media in respect to other pits in the volume. This indeed provides an apparatus for cell cultivation in which multiple different growth experiments can be done simultaneously to obtain statistically relevant results.

Optionally, the feeder part of the two or more pits has a feeder volume enclosed by an diameter of the first end ranging between 0.2 to 3.0 millimetre and a diameter of the second end ranging between 0.1 to 1.5 millimetre and a height ranging between 0.1 to 3.0 millimetre forming a conical funnel with an angle ranging between 45 to 80 degrees with respect to a base of the common volume, and wherein the feeder part terminates in the base part of the two or more pit. For example, the diameter of the first end of the feeder part is typically from 0.2, 0.3, 0.4, 0.5, 1.0, 1.5, 2.0 or 2.5 millimetre (mm) up to 0.3, 0.4, 0.5, 1, 1.5, 2, 2.5 or 3.0 mm, the diameter of the second end of the feeder part is typically from 0.1, 0.2, 0.3, 0.4, 0.5, 0.7, 0.9, 1.1 or 0.3 mm up to 0.2, 0.3, 0.4, 0.5, 0.7, 0.9, 1.1, 1.3 or 1.5 mm, the height of the feeder part is typically from 0.1, 0.2, 0.3, 0.4, 0.5, 0.6, 0.7, 0.8, 0.9, 1.0, 1.2, 1.4, 1.6, 1.8, 2.0, 2.2, 2.4, 2.6 or 2.8 mm up to 0.2, 0.3, 0.4, 0.5, 0.6, 0.7, 0.8, 0.9, 1.0, 1.2, 1.4, 1.6, 1.8, 2.0, 2.2, 2.4, 2.6, 2.8 or 3.0 mm. As a result, the volume of the conical cross-section of the feeder part attributed by the first and second ends of the feeder part and the height therebetween is typically from 0.032, 5.47 or 16.64 cubic millimetre (mm$^3$) up to 5.47, 16.64 or 27.23 mm$^3$.

Optionally, the angle ($\alpha$) of the conical funnel of the feeder part with respect to the base of the common volume of the first reservoir structure and the second reservoir structure is typically from 45, 50, 55, 60, 65, 70 or 75 degrees up to 50, 55, 60, 65, 70, 75 or 80 degrees. The steep wall angle as well as the optimum height of the feeder part enables the biological sample to be provided (namely, loading) to the desired location, preferably the base part of the two or more pits, preventing the biological sample from snagging (or sticking) on the sides of the feeder part.

Optionally, the base part of the two or more pits has a base volume enclosed by a height ranging between 0.1 to 0.5 millimetre and a diameter ranging between 0.2 to 2.0 millimetre, and wherein the base a diameter of the base part increases from the second end of the feeder part towards the second end of the base part. For example, the diameter of the base part is typically from 0.2, 0.4, 0.6, 0.8, 1.0, 1.2, 1.4, 1.6 or 1.8 millimetre (mm) up to 0.4, 0.6, 0.8, 1.0, 1.2, 1.4, 1.6, 1.8 or 2.0 mm preferably from 0.1, 0.2, 0.3, 0.4, 0.5, 0.6, 0.7, 0.8 or 0.9 mm up to 0.2, 0.3, 0.4, 0.5, 0.6, 0.7, 0.8, 0.9 or 1.0 mm, and the height of the base part is typically from 0.1, 0.2, 0.3 or 0.4 mm up to 0.2, 0.3, 0.4 or 0.5 mm. It will be appreciated that the diameter of the base part is equal to or lesser than twice the diameter of the second end of the feeder part, i.e. 0.1 to 1.0 mm. As a result, the volume of the base part attributed by a first end of the base part (coinciding with the second end of the feeder part as mentioned above) and the second end of the base part has diameter as aforementioned, and the height therebetween is typically from 0.00728, 0.985 or 2.21 cubic millimetre (mm$^3$) up to 0.985, 2.21 or 2.19 mm$^3$. Optionally, the volume enclosed by said diameters and heights of the various parts of each of the two or more pits may correspond to a multitude of shapes. However, said multitude of shapes should allow for expansion and accommodation of the biological sample in the base part during growth, while still maintaining the flow of the culture media and one or more analytes therethrough to keep the cells alive.

A technical effect of the above mentioned dimensions is that it has been found out to provide good culturing conditions when culturing organoids. The structure keeps the organoid and its subsequent expanded culture in place. Dimensions are important in terms of the size of an organoid to fit through the funnel and not be dislodged after culturing. This also has been found out to reduce culturing time in respect to structures which for example do not have similar structure of a base part. Also having a larger area on the bottom of the (for example half-spherical) base part allows for higher rates of perfusion. Thus we grow the organoids to larger sizes. Furthermore organoids confined to the culture-pits, prevents fall out during handling the apparatus and for example when the apparatus is turned around during processing. This allows for confining in a pliable pit for in-vivo like compression force. The disclosed pit design of a half-spherical shape, allows the retaining of a single organoid within the base part and also allows for ease of harvesting the cultured organoids if desired. Optionally the pit's inner surfaces can be treated either to prevent cell adhesion and promote spheroid forming or alternatively the pit's inner surfaces can be treated to enhance cell adhesion. One example of treating is coating.

Optionally, the number of pits is four or more. In such optional embodiments the four or more pits are arranged in form of an array unit selected from one of: a square array unit or a hexagonal array unit. It will be appreciated that when the number of pits is more than one such as four or more, the pits are can be arranged in form of the array unit. Specifically, four or more pits are arranged in rows which can be arranged in an array unit selected from a square array unit or a hexagonal array unit. For example, a 2×2 matrix comprising 4 pits, a 3×3 matrix comprising 9 pits, a 4×4 matrix comprising 16 pits, and so forth. Optionally, a hexagonal array comprises six or more pits in the pitted reservoir. In an example, the pits are arranged in a square array unit of a 4×4 matrix comprising 16 pits in the pitted reservoir.

Optionally, the pits are arranged to fit a square array unit of length ranging between 6 to 15 mm. For example, the length of each side of the square array unit can be from 6, 7, 8, 9, 10, 11, 12, 13 or 14 mm up to 7, 8, 9, 10, 11, 12, 13, 14 or 15 mm. Moreover, each square array unit may comprise 4 to 900 pits forming a square array unit of said pits. For example, the number of pits to fit a square array unit of aforesaid dimensions can be from 4, 40, 80, 120, 160, 200, 300, 400, 500, 600, 700 or 800 up to 40, 80, 120, 160, 200, 300, 400, 500, 600, 700, 800 or 900. In an example, the length of each side of the square array unit is 6.5 mm with 16 pits. Furthermore, said square array unit is surrounded by a wall of a height ranging between 1 to 10 mm and thickness ranging between 0.5 to 3.0 mm. According to an embodiment the pit geometry is arranged to be identical/similar to pixel layouts in commercial camera (for example CMOS or CCD) sensors. This way it is possible to couple a lens-free imaging system for pixel-level readout.

Optionally, the two or more pits of the first and the second reservoir structure a may be arranged in array units similar to or different from each other in size, shape, number and orientation. For example, pits of the pitted reservoirs of the first reservoir structure is a square array of 4×4 matrix comprising 16 pits having conical cross-section, whereas the pits of the pitted reservoirs of the second reservoir structure is a hexagonal array unit comprising 7 pitted reservoirs having a cylindrical cross-section.

Optionally, the two or more pits has one of: a conical cross-section, a cylindrical cross-section, a spherical cross-section, an elliptical cross-section, a polygonal shape. Optionally, the feeder part of the two or more pits is in a shape of a conical frustrum. Optionally, the base part of the two or more pits is in a shape of a frustrum or sphere. More optionally, the bottom of the base part may have a flat bottom, a bottom with minimal rounded edges, a V-shaped bottom or a U-shaped bottom. For sake of clarity, it is good to note, that the mentioned shapes refer to corresponding cross section of a 3d shape.

It will be appreciated that the diameter of the second end of the feeder part and the cross-section of the base part is larger than the diameter of the biological sample to enable proper loading of the biological sample at the bottom of the base part without risking the structural and functional integrity of the biological sample. Furthermore, the size of the biological sample is a function of a size of the cell(s), a cell number, and an amount of matrix or polymers in the biological sample.

Optionally, the feeder part of the two or more pits terminates in a shaft. The shaft is defined by a length ranging between 0.1 to 0.5 millimetre and a diameter, similar to the diameter of the second end of the feeder part, ranging between 0.1 to 1.0 millimetre. For example, the length of the shaft may typically be 0.1, 0.2, 0.3 or 0.4 millimetre (mm) up to 0.2, 0.3, 0.4 or 0.5 mm, and the diameter of the shaft may typically be 0.1, 0.2, 0.3, 0.4, 0.5, 0.6, 0.7, 0.8 or 0.9 mm up to 0.2, 0.3, 0.4, 0.5, 0.6, 0.7, 0.8, 0.9 or 1.0 mm. As a result, the shaft encloses a volume in a range of 0.00314 to 1.57. In an example, the volume enclosed by the shaft may typically be from 0.00314, 0.33 or 0.80 up to 0.33, 0.80 or 1.57 mm$^3$. Said shaft terminates in the base part of the two or more pits. The base part having a first end having a cross-section similar to that of the shaft and a diameter equal to lesser than twice the diameter of the second end of the feeder part or the shaft to enable effective growth of the biological sample therein.

In such case, preferably according to an example embodiment, the diameter of the first end of the feeder part, i.e. larger diameter, is 1.0 mm, the diameter of the second end of the feeder part, i.e. smaller diameter, is 0.3 mm, the height therebetween (i.e. height between the first end of the feeder part and the second end of the feeder part) is 1.0 mm, the angle (α) of the conical funnel of the feeder part with respect to the base of the common volume of the first reservoir structure and the second reservoir structure is 70.7 degrees, the height of the shaft part is 0.3 and diameter (corresponding to the smaller diameter of the feeder part and the smaller diameter of the base part) of the shaft part 0.3 mm, the diameter of the base part is 0.5 mm and the height of the base part, i.e. the height between the first end of the base part and the second end of the base part, is 0.2 mm. In deed such dimensions have been found to be particularly good for the growth Optionally, each of the pitted reservoirs of the first matrix of pitted reservoirs is connected via a respective microfluid channel to a gradient generator, wherein the gradient generator is configured to control a flow rate of one or more analytes to each of the pitted reservoirs of the first reservoir structure. The term "gradient" as used herein refers to concentrations of one or more analytes supplied for analysing effect thereof on the biological sample. Specifically, the gradient is a measurement of how much the concentration of one or more analytes changes when supplied from one region (i.e. a microfluid reservoir) to another (i.e. a pitted reservoir). For example, the gradient may be of a concentration of 5 Molar (M, or moles per litre (mol/L)), 10 M, 100 M, 200 M, and so on. The term "gradient generator" as used herein refers to a means for producing such gradient, i.e. generating different concentrations of the one or more analytes for analysing effect thereof on the biological sample. Such gradient generator provides supply of the different concentrations of the one or more analytes from a region of higher concentration (such as the microfluid reservoir) to a region of lower concentration (such as the pitted reservoirs). In an example, the gradient generator may comprise a micropump. Optionally, the gradient generator is configured to control the flow rate of the different concentrations of one or more analytes to the pitted reservoirs of the first reservoir structure. More optionally, the control of flow rate is according to a user defined gradient function.

Optionally, the multiple layer architecture of the apparatus enables creation of concentration-dependent cross-correlation of one or more analytes. The one or more analytes are supplied to the corresponding pitted reservoirs of the first matrix of the pitted reservoirs. Optionally, the first matrix of the pitted reservoirs is arranged in a square array unit to measure two analytes. Optionally, the stacked arrangement of the first matrix of the pitted reservoirs, the second matrix of the pitted reservoirs on the either side of the membrane may receive different concentrations of the one or more analytes. More optionally, the one or more analytes that might adversely react with the culture media is supplied to the apparatus separately as different aliquots.

In an example, the apparatus may be a 3×3 square array unit of the first matrix of pitted reservoirs and the second pitted reservoirs on the either side of the membrane. Each of the pitted reservoirs comprise 9 pits for cultivating 9 biological samples in each pitted reservoir, simultaneously. The apparatus comprises two gradient generators, i.e. gradient generator A and gradient generator B, having a gradient of an analyte 'A' and a gradient of an analyte 'B', respectively. The gradient generator A has a dilution ratio of 1:10:100, wherein each of the vertical columns of the square array unit receives a different concentration of the analyte A, while each of the pitted reservoir of a vertical column of the square array unit receives a same concentration of the analyte A. The gradient generator B has a dilution ratio of 1:3:9, wherein each of the horizontal rows of the square array unit receives a different concentration of the analyte B, while each of the pitted reservoir of each horizontal row of the square array unit receives a same concentration of the analyte B. For example, with a starting concentration of 1M (moles per litre (mol/L)) for each analytes A and B, each of the pitted reservoir of the square array unit receives the following concentrations of the analytes A and B:

TABLE 1

Analyte concentrations from a dual gradient generator with a 1:10:100 gradient of analyte A in the columns and a 1:3:9 gradient of analyte B in the rows of a 3 × 3 matrix of pitted reservoirs

| | | |
|---|---|---|
| A 1M, B 1M | A 0.1M, B 1M | A 0.01M, B 1M |
| A 1M, B 0.33M | A 0.1M, B 0.33M | A 0.01M, B 0.33M |
| A 1M, B 0.11M | A 0.1M, B 0.11M | A 0.01M B 0.11M |

Herein, the gradient generator A comprises an inlet for culture media and an inlet for the analyte A. The gradient generator A is configured to provide a first concentration of the analyte A to a first microfluid channel, a second concentration of the analyte A to a second microfluid channel, and a third concentration of the analyte A to a third microfluid channel. The first microfluid channel forms a channel between the gradient generator A and one or more pitted reservoirs of a first horizontal row to provide the first concentration of the analyte A thereto. Similarly, the second microfluid channel and the third microfluid channel form a channel between the gradient generator A and a different set of one or more pitted reservoirs of a second horizontal row and a third horizontal row to provide the second concentration of the analyte A and the third concentration of the analyte A thereto, respectively.

Similarly, the gradient generator B comprises an inlet for culture media and an inlet for the analyte B. The gradient generator B is configured to provide a first concentration of the analyte B to a fourth microfluid channel, a second concentration of the analyte B to a fifth microfluid channel, and a third concentration of the analyte B to a sixth microfluid channel. The fourth microfluid channel forms a channel between the gradient generator B and one or more pitted reservoirs of a first vertical column to provide the first concentration of the analyte B thereto. Similarly, the fifth microfluid channel and the sixth microfluid channel form a channel between the gradient generator B and a different set of one or more pitted reservoirs of a second vertical column and of a third vertical column to provide the second concentration of the analyte B and the third concentration of the analyte B thereto, respectively.

It will be appreciated that the multiple layer architecture of the apparatus comprises a plurality of gradient generation layers. The plurality of gradient generation layers results in a cross-gradient of a plurality of gradient generators and microfluidic channels corresponding to the different gradients of one or more analytes. Such gradient generation layers enable two or more liquids containing one or more substances, such as the culture media and one or more analytes, to be perfused in such a manner as to form a cross-gradient between said two liquids and or the substances they contain.

Optionally, the biological sample is grown into a three-dimensional cell culture on the membrane facing the base part of the two or more pits. The membrane provides an optimum substrate for the biological sample to bind to. The biological sample has an innate mechanism to grow by multiplying cells in optimum conditions of growth. The culture media and the apparatus provide such optimum conditions, for example, suitable temperature, pH, nutrients, moisture, gaseous exchange, and so forth, for the growth of the biological sample. It will be appreciated that the pore size of the membrane is smaller than the size of the biological sample. A smaller pore size prevents the biological sample from passing through the membrane and thereby sticking at the membrane to grow. The biological sample, when incubated, under the optimum growth conditions grow in all three dimensions of space available for growth. The volume and cross-section of the base of the pit and the fabrication material of the membrane and the apparatus allows for effective growth of the three-dimensional cell culture.

Optionally, the biological sample is selected from any one of: a cell, a tissue, a spheroid, an organoid, a cell line, a monolayer cultured cells, cells embedded in a matrix, an organ, a microorganism culture or a combination thereof, and wherein size of the biological sample ranges between 50 to 300 micrometre. The biological sample is selected from a group of cells having a growth rate. The biological sample is isolated from its natural environment under optimum conditions. Optionally, the methods of isolation of the biological sample is selected from conventional methods of cell isolation, known in the art. Typically, the size of the biological sample may be from 50, 100, 150, 200 or 250 micrometres (μm) up to 100, 150, 200, 250 or 300 μm. It will be appreciated that the biological sample may be a single cell or multiple cells.

Optionally, the apparatus is used for at least one of: cultivating a single biological sample, co-cultivating of a plurality of biological samples, and analysing the effects of one or more analytes in the cross-gradient flow on the cell cultures of biological samples. More optionally, the apparatus may be used as a single apparatus for cultivating a single biological sample. The term "single apparatus" refers to an apparatus having only a first reservoir structure with or without a membrane at the bottom layer of the apparatus. For co-cultivating a plurality of biological samples, two such single apparatuses are adjoined together with a porous membrane in between. Such stacked arrangement creates a novel apparatus (or device) for culturing different combinations of cells and organoids. For instance, the two or more pits of the first matrix of pitted reservoirs of the first reservoir structure can house organoids or spheroids, while the two or more pits of the second matrix of pitted reservoirs of the second reservoir structure, arranged opposite the first reservoir structure, can house another type of spheroid or organoid, monolayer cultured cells, or cells embedded in a matrix such as collagen, hydrogel or other such matrix.

Optionally, the apparatus comprises a guiding element (or tab) for easy handling, placement and removal of the apparatus from the multi-well cell culture plate. Optionally, the apparatus comprises a microbial barrier preventing the growth of microbial and/or viral contamination during growth and storage of cells.

In an example, the multiple-layer architecture of the apparatus has four layers, i.e. a first layer, a second layer, a third layer and a fourth layer, each having a predefined first, second, third and fourth thickness, respectively. The first layer and the second layer of the apparatus combine to form the first reservoir structure, and the third layer and the fourth layer of the apparatus combine to form the second reservoir structure. The first layer of the apparatus holds the common volume of the first matrix of pitted reservoirs of the first reservoir structure and the fourth layer of the apparatus holds the common volume of the second matrix of pitted reservoirs of the second reservoir structure. The first reservoir structure and second reservoir structure are arranged symmetrically with respect to a membrane, arranged in between the second layer and the third layer of the apparatus. Such symmetrical arrangement of the first and the second reservoir structures further results in aligning of the second opening of the first matrix of pitted reservoirs with the third opening of the second matrix of pitted reservoirs.

Moreover, the first layer of the apparatus holds the microfluid channels integrated therein. The microfluid channel has an opening in the first layer of the apparatus to supply the culture media and one or more analytes, in same or different concentrations thereof, when in operation. When in operation, the culture media and one or more analytes of a predefined concentration is received in the first matrix of pitted reservoirs from at least one gradient via the respective microfluid channel. The one or more analytes of a predefined concentration may be received in the common volume of the first matrix of pitted reservoirs at the same time or flow thereof may be controlled as per the user's requirements.

Furthermore, the culture media and one or more analytes fills the first volume of the first reservoir structure in the first layer to a level, i.e. a top of the common volume. Furthermore, the first layer of the apparatus is arranged with the second layer of the apparatus comprising two or more pits, thereby supplying the culture media and one or more analytes from the base of the common volume in the first layer to the first end of the two or more pits in the second layer of the apparatus with the help of gravity. The second end of the two or more pits in the second layer of the apparatus faces the membrane. The membrane enables flow of the culture media and one or more analytes from the second end of the two or more pits through the membrane and into the third layer and the fourth layer of the apparatus comprising two or more pits of the second pitted reservoir and the common volume of the second matrix of pitted reservoirs.

It will be appreciated that the second reservoir structure has a form factor similar to that of the first reservoir structure with respect to the second matrix of pitted reservoirs. In other words, the second reservoir structure has the second matrix of pitted reservoirs comprising two or more pits and enclosing a common volume and a pit volume thereof similar to the first reservoir structure having the first matrix of pitted reservoirs comprising two or more pits and enclosing a common volume and a pit volume thereof. Said arrangement of the first and the second reservoir structures enable growth of the biological sample in all the three dimensions of space at the base of the first and the second matrix of pitted reservoirs.

The present disclosure also relates to the method as described above. Various embodiments and variants disclosed above, with respect to the aforementioned first aspect, apply mutatis mutandis to the method.

The method of the present disclosure comprises providing a first biological sample to a base part of two or more pit of a second matrix of pitted reservoirs of a second reservoir structure. The term "first biological sample" refers to a biological sample provided at a first instant of time to initiate the process achieved by use of the afore-mentioned apparatus for cell cultivating. The first biological sample is provided to the base part of two or more pits of the second matrix of pitted reservoirs of the second reservoir structure. It will be appreciated that the placement of the biological sample is at a bottom-most part of the base part adjacent to the second face of the membrane facing the base part of two or more pits of the second matrix of pitted reservoirs of the second reservoir structure. The first biological sample may be provided by, for example, micropipettes.

Furthermore, the method comprises providing a first predefined amount of culture media to the first biological sample. The second reservoir structure containing the first biological sample is perfused with the first predefined amount of culture media. The culture media comprises essential nutrients, growth media, hormones, antibiotics, and so forth for enabling effective growth of the first biological sample. The first predefined amount of culture media refers to an amount of culture media required to fill the second matrix of pitted reservoirs for growth of the first biological sample. The culture media is changed in the second reservoir structure after every 2 days. The change of culture media ensures proper nutrition to the growing cells and keeping cells alive for a longer period of time. Notably, the second reservoir structure has no microfluid channel for transfer of one or more analytes.

Furthermore, the method comprises incubating the provided first biological sample for a first incubation time period to produce a first three-dimensional cell culture at a membrane facing the base part of the two or more pits of the second matrix of pitted reservoir. The first biological sample is grown in the first predefined amount of culture media for the first incubation period for example, of 4 days, in the second matrix of pitted reservoirs. Said period of growth results in generation of the first three-dimensional cell culture on the second face of the membrane. As mentioned earlier, the three-dimensional cell culture results from growth of the first biological sample in all the three dimensions of space. It will be appreciated that due to the smaller pore size of the membrane with respect to the size of the first biological sample, the first biological sample or the resultant first three-dimensional cell culture adheres to the membrane and is unable to pass therethrough.

Furthermore, the method comprises reversing an orientation of the second reservoir structure. It will be appreciated that to reverse the orientation of the second reservoir structure, the apparatus is to be upturned. Therefore, after the first incubation period, the second reservoir structure is turned upside down. It will be appreciated that reversing the orientation of the second reservoir structure results in complete flow-out of the culture media therefrom, leaving only the first three-dimensional cell culture adhered on the second face of the membrane.

Furthermore, the method comprises providing a second biological sample to a base part of two or more pits of a first matrix of pitted reservoirs of a first reservoir structure, wherein the first reservoir structure is arranged to be opposite to the second reservoir structure. Upon reversing the orientation of the second reservoir structure in the previous step, the first reservoir structure arranged opposite to the second reservoir structure on other side of the membrane is exposed to the user. As mentioned earlier, the first reservoir structure, the second reservoir structure and the membrane are stacked such that the second surface of the first reservoir structure faces the first face of the membrane and the third surface of the second reservoir structure faces the second face of the membrane. Specifically, the second surface of the first reservoir structure is opposite the third surface of the second reservoir structure. Furthermore, the second opening on the second surface of the first reservoir structure and the third opening on the third surface of the second reservoir structure to couple together the first volume and second volume.

The term "second biological sample" refers to a biological sample provided at a second instant of time to continue the process achieved by use of said apparatus for cell cultivating. The second biological sample is provided to the base part of two or more pits of the first matrix of pitted reservoirs of the first reservoir structure. It will be appreciated that the placement of the biological sample is at a bottom-most part of the base part adjacent to the first face of the membrane facing the base part of two or more pits of the first matrix of pitted reservoirs of the first reservoir structure. The second biological sample may be provided using, for example, micropipettes. Optionally, the first reservoir structure receives the second biological sample via the first surface of the first reservoir structure.

Optionally, the second biological sample is same as or different from the first biological sample. In an example, the second biological sample is the same cells type as that of the first biological sample. For example, both the first and second biological sample may be monolayer cultured cells or spheroids or organoids. In another example, the second biological sample is different from the first biological sample. For example, the first biological sample is monolayer cultured cells and the second biological sample may be cells embedded in a matrix such as collagen, hydrogen, and so on, or other type of spheroids or organoids.

Furthermore, the method comprises providing a second predefined amount of culture media via an inlet for the culture media to the second biological sample. The first reservoir structure containing the second biological sample is perfused with a second predefined amount of culture media. The culture media comprises essential nutrients, growth media, hormones, antibiotics, and so on for enabling effective growth of the first biological sample. The second predefined amount of culture media refers to an amount of culture media required to be supplied to the first matrix of pitted reservoirs continuously for growth of the second biological sample. It will be appreciated that the second predefined amount of culture media flows past the second biological sample, the membrane and the first three-dimensional cell culture opposite the second biological sample. Moreover, such continuous supply of the second predefined amount of culture media ensures proper nutrition to the growing cells and keeping cells alive for a longer period of time on the either side of the membrane.

Furthermore, the method comprises incubating the provided second biological sample for a second incubation time period to produce a second three-dimensional cell culture at the membrane facing the base part of the two or more pits of the first matrix of pitted reservoirs. The second biological sample is grown in the second predefined amount of culture media for the second incubation period for example, of 2-4 days, in the first matrix of pitted reservoirs. Said period of growth results in generation of the second three-dimensional cell culture on the first face of the membrane. It will be appreciated that due to the smaller pore size of the membrane with respect to the size of the second biological sample, the second biological sample or the resultant second three-dimensional cell culture adheres to the membrane and is unable to pass therethrough.

Furthermore, the method comprises providing one or more analytes to the first matrix of pitted reservoirs. Optionally, one or more analytes are stored in one or more analyte reservoirs and supplied to the first matrix of pitted reservoirs via the microfluid channel. The one or more analytes flow into each of the two or more pits of the first matrix of pitted reservoirs through a respective integrated microfluid channel. Optionally, the one or more analytes is selected from any of: a pharmaceutical product, a toxin, or a pollutant. The one or more analytes is supplied to the two or more pits to analyse the effect of said one or more analytes on the first three-dimensional cell culture, the second three-dimensional cell culture, or both of the first and second three-dimensional cell cultures.

Optionally, the method comprises providing one or more analytes to the first matrix of pitted reservoirs in varying concentrations. The varying concentrations of one or more analytes are provided to the first matrix of pitted reservoirs from the gradient generator via a respective microfluid channel. One or more microfluid channels are configured to provide varying concentrations of one or more analytes to the one or more pitted reservoirs of the first matrix of pitted reservoirs.

Optionally, the method further comprises controlling a flow rate of one or more analytes to the first matrix of pitted reservoirs. The flow rate of one or more analytes is controlled by a cross-gradient formed by a plurality of gradient generators and microfluid channels corresponding to each pitted reservoir of the first matrix of pitted reservoirs. Optionally, the microfluid channel is configured to provide different flow rates of the one or more analytes in corresponding pitted reservoirs. Notably, the different flow rate of the culture media and one or more analytes flowing through said microfluid channel corresponds to a fabrication material of the microfluid channel, a thickness of the fabrication material of the microfluid channel, a viscosity of the culture media and one or more analyte, concentrations of the one or more analytes, and so forth.

DETAILED DESCRIPTION OF THE DRAWINGS

Referring to FIG. 1, there is shown a cross-section of an apparatus 100 for cell cultivation, in accordance with an embodiment of the present disclosure. The apparatus 100 comprises a first reservoir structure 102, a second reservoir structure 104 and a membrane 106. Moreover, the apparatus 100 has a multilayer architecture formed from a first layer 108, a second layer 110, a third layer 112 and a fourth layer 114. The first layer 108 and the second layer 110 combine to form the first reservoir structure 102. The third layer 112 and the fourth layer 114 form the second reservoir structure 104. The first reservoir structure 102 has a first matrix of pitted reservoirs 116. The second reservoir structure has a second matrix of pitted reservoirs 118. The first reservoir structure 102, the second reservoir structure 104 and the membrane 106 are arranged as a stack, wherein the membrane 106 is arranged between the first reservoir structure 102 and the second reservoir structure 104 and the first matrix of pitted reservoirs 116 is aligned with a second matrix of pitted reservoirs 118 to couple pitted reservoirs 116A and 116B of the first matrix of pitted reservoirs 116 together with the pitted reservoirs 118A and 118B of the second matrix of pitted reservoirs 118, respectively via the membrane 106.

Moreover, the pitted reservoirs 116A, 116B, 118A and 118B comprise a common volume and a pit volume, as illustrated in FIG. 1 with respect to pitted reservoir 116B, the common volume 120 and pit volume 122.

The pit volume 122 comprises of two or more pits 124. The common volume 120 comprises one or more openings 126 for microfluid channel 128. Furthermore, each of the pitted reservoirs 116A and 116B of the first matrix of pitted reservoirs 116 is connected via a respective microfluid channel 128 to a gradient generator 130, wherein the gradient generator 130 is configured to control a flow rate of one or more analytes to the each pitted reservoirs 116A and 116B of the first reservoir structure 102.

Figure 2:
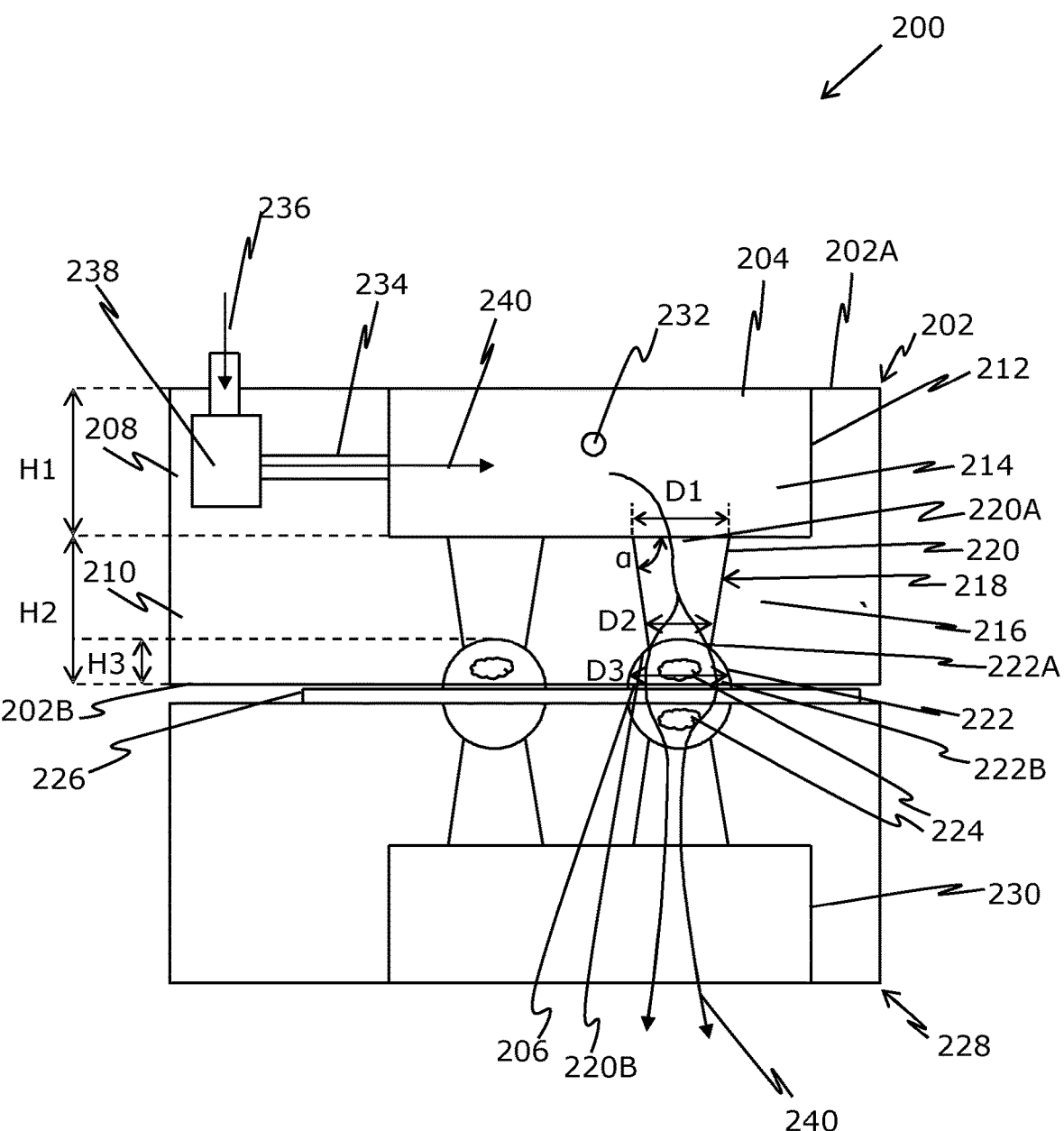

Referring to FIG. 2, there is shown a cross-section of an apparatus 200 for cell cultivation, in accordance with an embodiment of the present disclosure. The apparatus 200 comprises a first reservoir structure 202 comprising a first surface 202A and a second surface 202B. The first reservoir structure 202 has a first opening 204 on the first surface 202A and a second opening 206 on the second surface 202B. The first reservoir structure 202 can be manufactured from a first layer 208 having thickness of H1 and a second layer 210 having thickness of H2. The first reservoir structure 202 has a first matrix of pitted reservoirs 212.

The first matrix of pitted reservoirs 212 comprises a common volume 214 and a pit volume 216. The pit volume 216 comprises of two or more pits, such as the pit 218. The pit 218 comprises a feeder part 220, connected to the common volume 214 via a first end 220A of the feeder part 220, and a base part 222, connected to a second end 220B of the feeder part 220 via a first end 222A of the base part 222. The feeder part 220 has an angle α with respect to the base of the common volume 214. The first end 220A of the feeder part 220 has a diameter of D1. The height of the feeder part 220 is equal to a difference of the thickness H2 of the second layer 210 and a height H3 of the base part 222. The second end 220B of the feeder part 220 has diameter D2. The first matrix of pitted reservoirs 212 comprises a first opening coinciding with the first opening 204 on the first surface 202A of the first reservoir structure 202 via which a biological sample 224 can be provided to the base part 222. The base part 222 has an opening (not shown) of a diameter D3 at a second end 222B of the base part 222 facing the membrane 226 and the base part 222 is configured to accommodate the biological sample 224 for three-dimensional cell cultivation when in use.

A second reservoir structure 228 has a similar second matrix of pitted reservoirs 230 opposite to the first matrix of pitted reservoirs 212 of the first reservoir structure 202. The first reservoir structure 202, the second reservoir structure 228 and the membrane 226 are arranged as a stack, wherein the membrane 226 is arranged between the first reservoir structure 202 and the second reservoir structure 228 and the first matrix of pitted reservoirs 212 is aligned with a second matrix of pitted reservoirs 230 to couple the volume enclosed therein via the membrane 226. An initial cultivation of the biological sample 224 is carried out in the second matrix of pitted reservoirs 230 for a predefined period of time.

The common volume 214 comprises one or more openings 232 for microfluid channel 234. When in operation, one or more analytes 236 of a first concentration is received by the first matrix of pitted reservoirs 212 from a first gradient generator 238 via a first microfluid channel 234. The one or more analytes 236 of a second concentration is received by the first matrix of pitted reservoirs 212 from a second gradient generator (not shown) via a second microfluid channel (not shown) through one or more openings 232. A fluid 240 comprising one or more analytes 236 and culture media flows past the growing biological sample 224 via the opening at a second end 222B of the base part 222 facing the membrane 226 and through the membrane 226 into the pit 218 of the second matrix of pitted reservoirs 230 opposite to the first matrix of pitted reservoirs 212 of the first reservoir structure 202.

Figure 3:
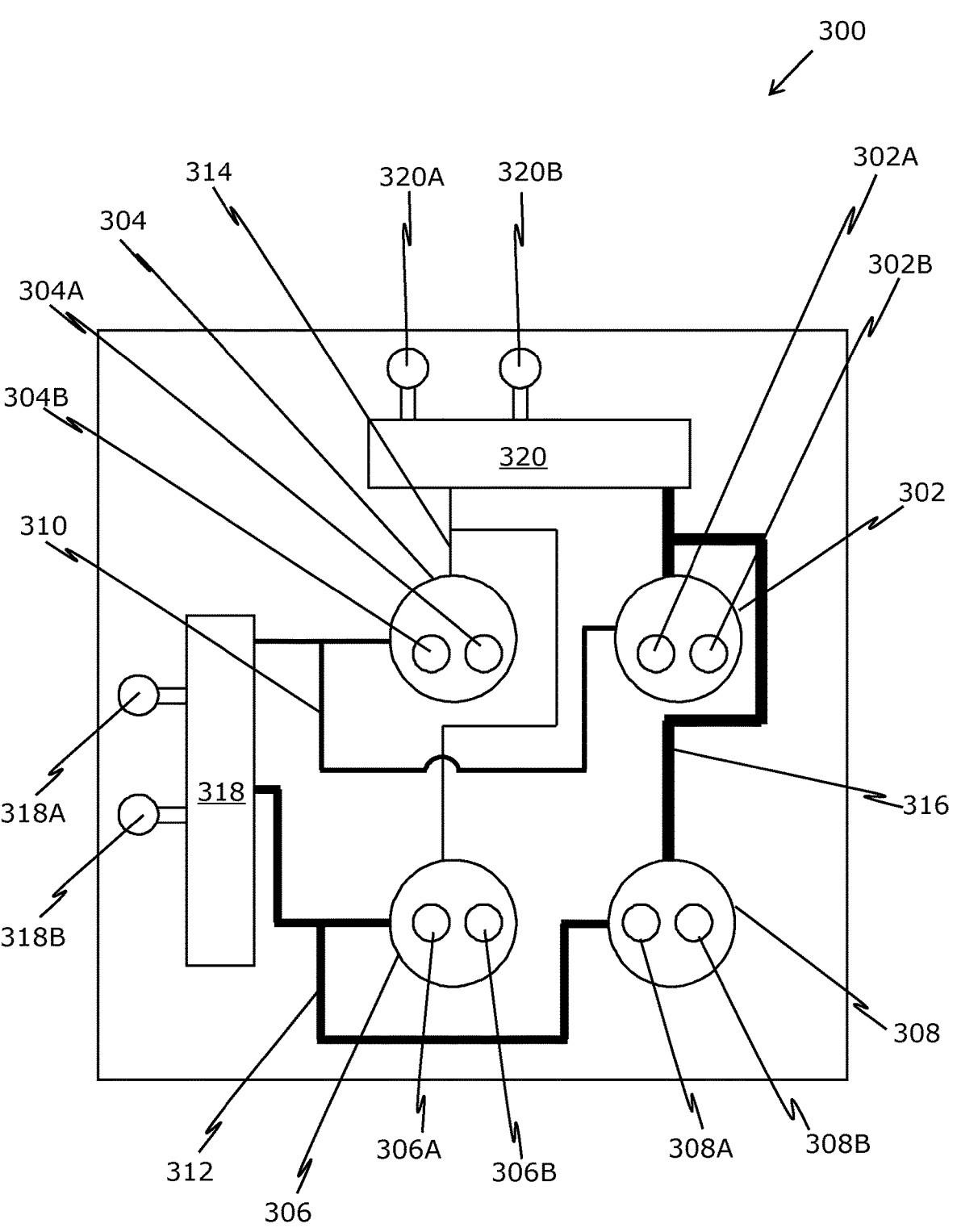
FIG. 3 is top view of the apparatus of FIG. 1, in accordance with an embodiment of the present disclosure.

Referring to FIG. 3, there is shown a top view of the apparatus 300 for cell cultivation, in accordance with an embodiment of the present disclosure. As shown, the apparatus 300 comprises a first matrix of pitted reservoirs comprising a first pitted reservoir 302, a second pitted reservoir 304, a third pitted reservoir 306 and a fourth pitted reservoir 308. Each of the pitted reservoirs 302, 304, 306 and 308 has two pits 302A and 302B, 304A and 304B, 306A and 306B, and 308A and 308B, respectively.

Each of the pitted reservoirs 302, 304, 306 and 308 has an opening facing the top of the apparatus 300. Each of the pitted reservoirs 302, 304, 306 and 308 is connected via microfluid channels 310, 312, 314 and 316 to a first gradient generator 318 and a second gradient generator 320 to receive one or more analyte and culture media mixture (not shown). Notably, the microfluid channels 310, 312, 314 and 316 are embedded in the apparatus 300.

The first gradient generator 318 has an inlet 318A for culture media and an inlet 318B for one or more analytes. The first gradient generator 318 is configured to provide to the first microfluid channel 310 a first concentration of a first analyte and to a second microfluid channel 312, a second concentration of the first analyte. The first microfluid channel 310 forms a channel between the gradient generator 318 and the first pitted reservoir 302 and the second pitted reservoir 304. As a result, the first concentration of the first analyte can be provided to the first pitted reservoir 302 and the second reservoir 304. The second microfluid channel 312 forms a channel between the gradient 318 and the third pitted reservoir 306 and the fourth pitted reservoir 308. As a result, the second concentration of the first analyte can be provided to the third pitted reservoir 306 and the fourth pitted reservoir 308.

The second gradient generator 320 has an inlet 320A for culture media and an inlet 320B for one or more analytes. The second gradient generator 320 is configured to provide to a third microfluid channel 314 a third concentration of a second analyte and to a fourth microfluid channel 316 a fourth concentration of the second analyte. The third microfluid channel 314 forms a channel between the second gradient generator 320 and the second pitted reservoir 304 and the third pitted reservoir 306. As a result, the third concentration of the second analyte can be provided to the second pitted reservoir 304 and the third pitted reservoir 306. The fourth microfluid channel 316 forms a channel between the second gradient generator 320 and the first pitted reservoir 302 and the fourth pitted reservoir 308. As a result, the fourth concentration of the second analyte can be provided to the first pitted reservoir 302 and the fourth pitted reservoir 308.

Figure 4:
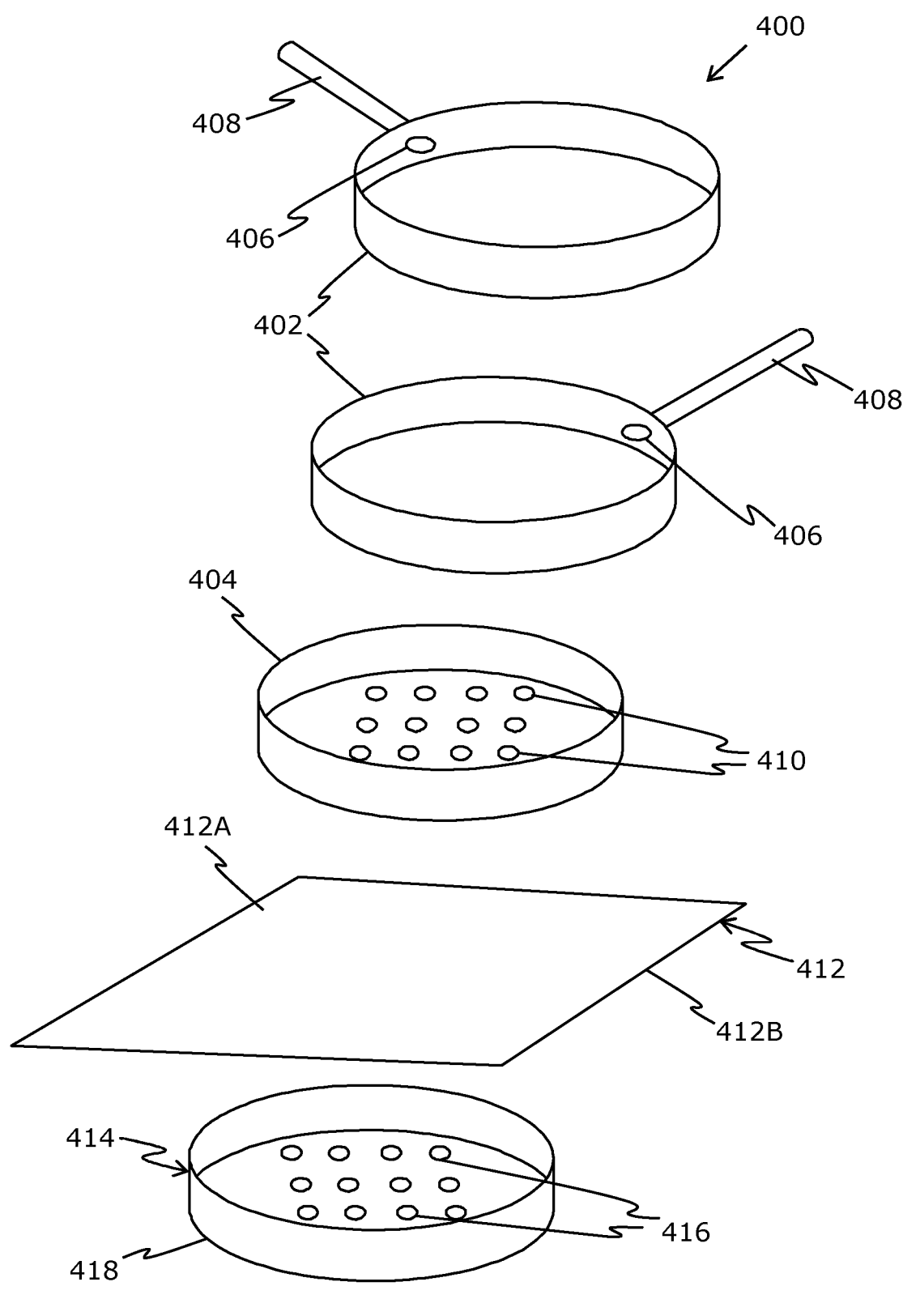
FIG. 4 is an exploded view of layers of a pitted reservoir, in accordance with an embodiment of the present disclosure.

Referring to FIG. 4, there is shown an exploded view of layers of a pitted reservoir 400, in accordance with an embodiment of the present disclosure. As shown, the pitted reservoir 400 comprises a common volume 402 and a pit volume 404. The common volume 402 comprises one or more openings 406 for a microfluid channel 408. The pit volume 404 comprises of two or more pits 410. Each of the two or more pits 410 comprises a feeder part (not shown), connected to the common volume 402, and a base part (not shown). The base part of each of the two or more pits 410 faces a first face 412A of a membrane 412. Another pitted reservoir 414 comprising two or more pits 416 in a pit volume 418 thereof can be placed facing a second face 412B of the membrane 412 opposite to the first face 412A. The pitted reservoir 400, the pitted reservoir 414 and the membrane 412 are arranged as a stack, wherein the membrane 412 is arranged therebetween.

Figure 5:
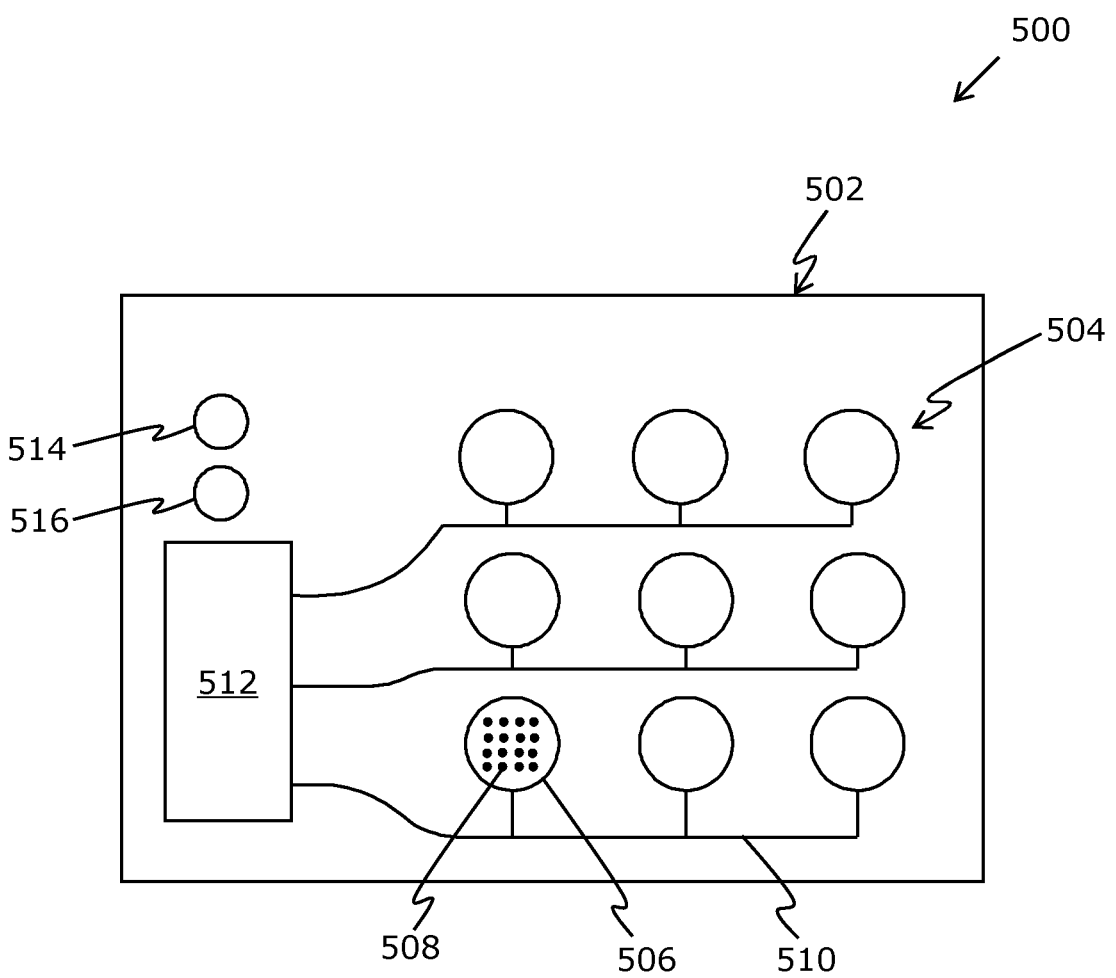
FIG. 5 is a schematic illustration of an apparatus, in accordance with an embodiment of the present disclosure.

Referring to FIG. 5, there is shown a schematic illustration of an apparatus 500, in accordance with an embodiment of the present disclosure. As shown, the apparatus 500 comprises a first reservoir structure 502 having a first matrix of pitted reservoirs 504. Furthermore, each of the pitted reservoirs, such as the pitted reservoir 506, comprise two or more pits, such as the pit 508, and is connected via a respective microfluid channel, such as the microfluidic channel 510, to a gradient generator 512. Moreover, the gradient generator 512 receives the culture media from an inlet 514 for culture media and one or more analytes from an inlet 516 for one or more analytes. The gradient generator 512 is configured to control a flow rate of one or more analytes to each of the pitted reservoirs 506 of the first reservoir structure 504.

Figure 6A:
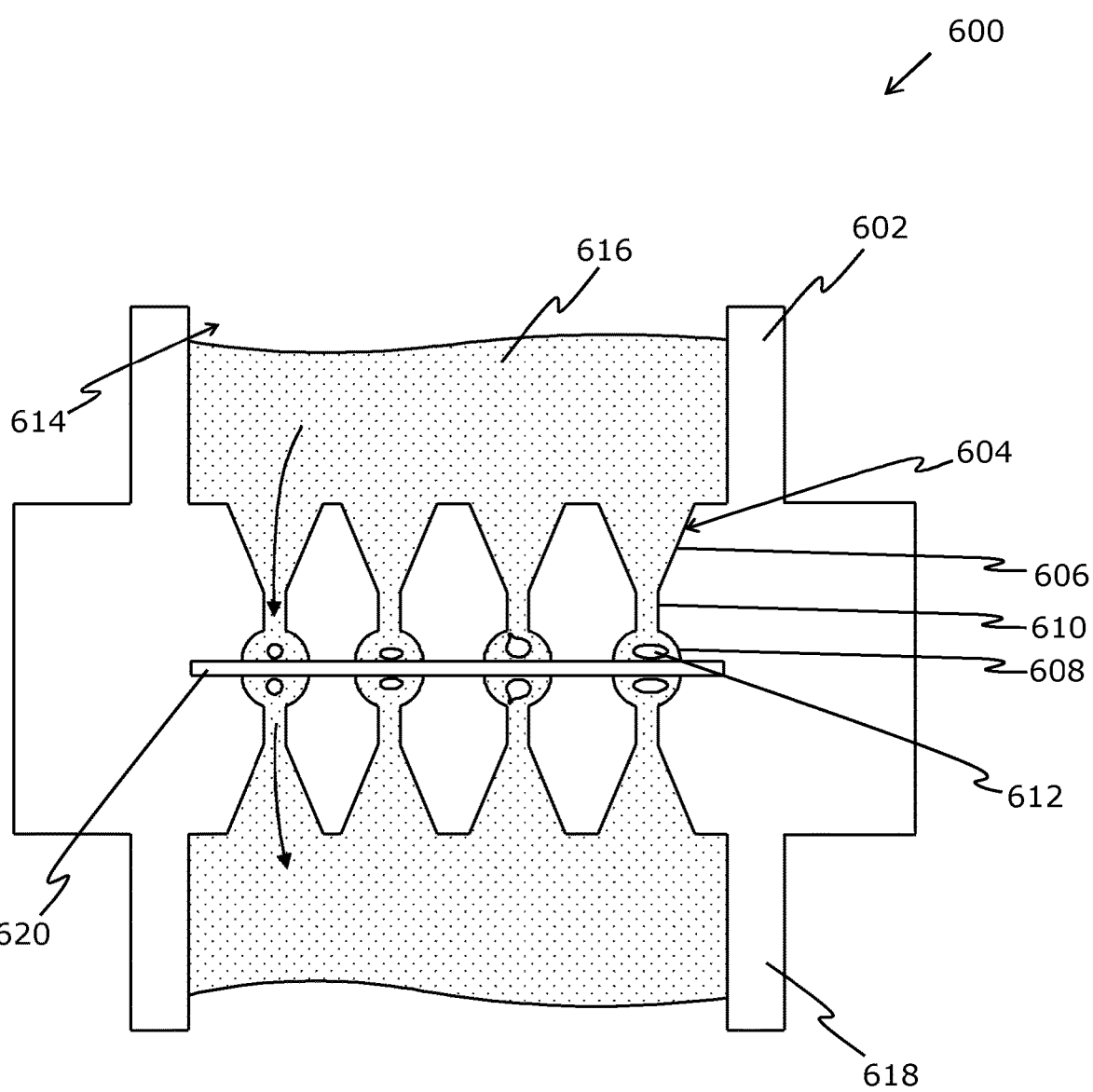
FIGS. 6A and 6B are illustrations of cross-section of an apparatus, in accordance with different implementations of the present disclosure.
Figure 6B:
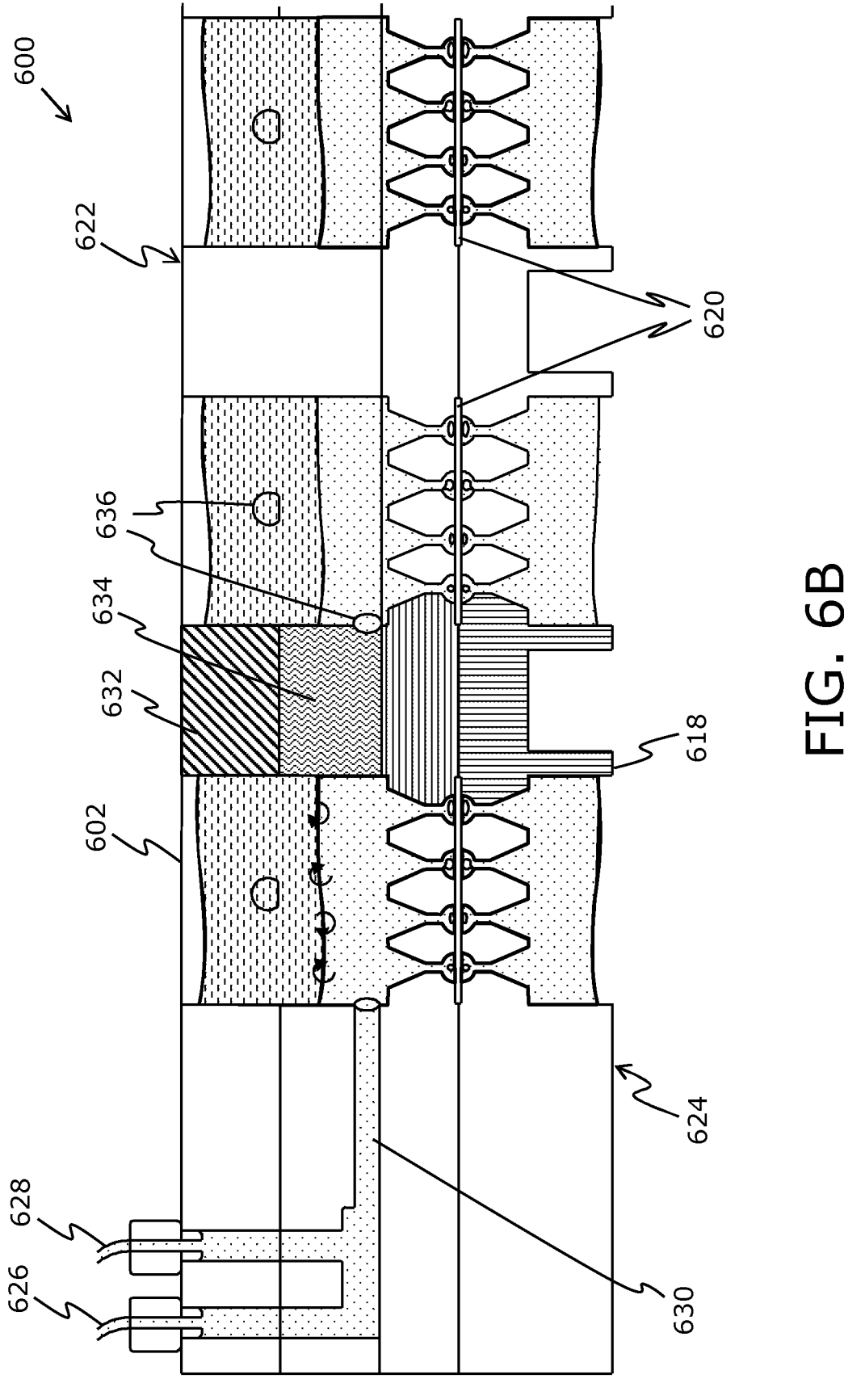

Referring to FIGS. 6A and 6B, there are shown illustrations of cross-section of an apparatus 600, in accordance with different implementations of the present disclosure. As shown in FIG. 6A, the apparatus 600 comprises the first pitted reservoir 602 comprising pits, such as a pit 604. Each of the pits, such as the pit 604, comprises a feeder part 606, a base part 608 and a shaft part 610 connecting the feeder part 606 and the base part 608. A biological sample 612 is provided to the bottom of the base part 608 from an opening 614 of the first pitted reservoir 602. Moreover, the first pitted reservoir 602 is perfused with fluid 616 comprising culture media and one or more analytes, when in operation. Furthermore, a second pitted reservoir 618 is arranged opposite to the first pitted reservoir 602 on the other side of a membrane 620. The fluid 616 flows past the biological sample 612 and passes through the membrane 620 into the second pitted reservoir 618. It will be appreciated that the configuration of pits in the second pitted reservoir 618 is similar to the first pitted reservoir 602 in terms of the pits.

As shown in FIG. 6B, the apparatus 600 comprises a first matrix of pitted reservoirs 622 and a second matrix of pitted reservoirs 624 aligned together via the membrane 620. The first matrix of pitted reservoirs 622 comprises a plurality of pitted reservoirs, such as the pitted reservoir 602 arranged in an array unit (shown here is an array unit of 3×1 lattice) and the second matrix of pitted reservoirs 624 comprises a plurality of pitted reservoirs, such as the pitted reservoir 618 arranged in an array unit (shown here is an array unit of 3×1 lattice). The apparatus further comprises an inlet 626 for culture media and an inlet 628 for one or more analytes. The inlet 626 for culture media and the inlet 628 for one or more analytes are coupled to a gradient generator (not shown).

Each of the pitted reservoirs, such as the pitted reservoir 602, of the first matrix of pitted reservoirs 622 is connected via a respective microfluid channel 630 to the gradient generator. The gradient generator is configured to control a flow rate of one or more analytes to each of the pitted reservoirs, such as the pitted reservoir 602, of the first matrix of pitted reservoirs 622. Moreover, the apparatus 600 is manufactured having a multilayer architecture comprising of a plurality of layers, such as a first layer 632 and a second layer 634. The at least one of the plurality of layers, such as the first layer 632 and the second layer 634, forming the common volume of the pitted reservoir, such as the pitted reservoir 602, of the first matrix of pitted reservoirs 622, comprises one or more openings 636 for the microfluid channel 630 into the pitted reservoir, such as the pitted reservoir 602, of the first matrix of pitted reservoirs 622. It will be appreciated that the apparatus 600 of FIGS. 6A and 6B may be used for three-dimensional cell cultivation of different types of biological sample 612, i.e. co-culturing of two or more biological samples.

Figure 7:
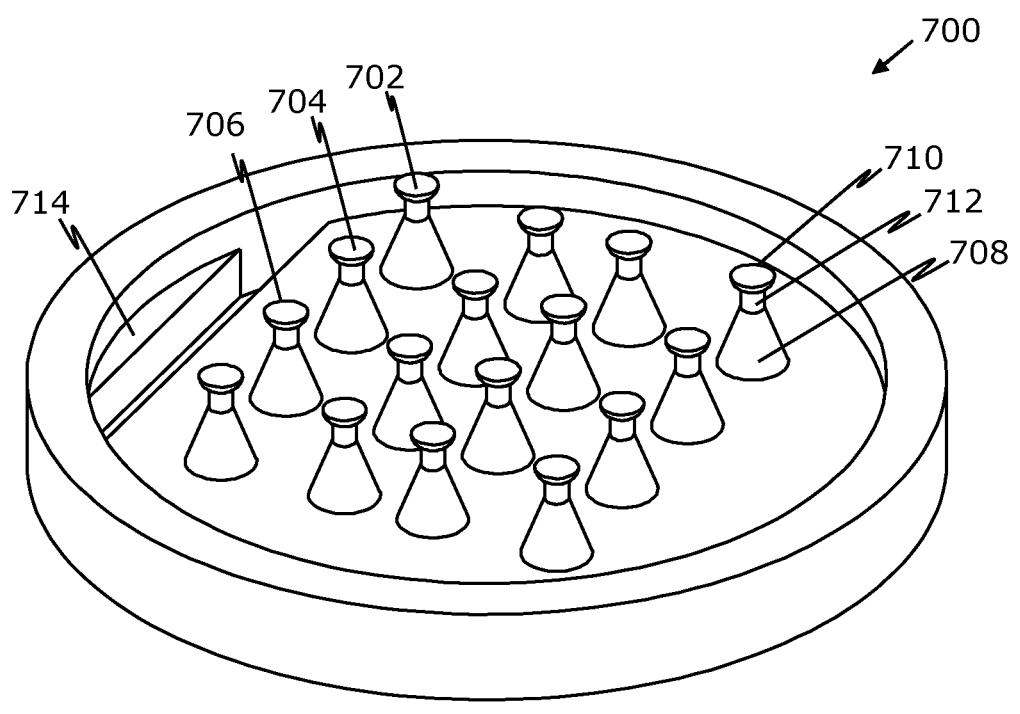
FIG. 7 is a schematic illustration of a mould for manufacturing a pitted reservoir, in accordance with an embodiment of the present disclosure.

Referring to FIG. 7, there is shown an illustration of a mould 700 for manufacturing a pitted reservoir (such as the pitted reservoir 800), in accordance with an embodiment of the present disclosure. As shown, the mould 700 comprises 16 protrusion such as protrusions 702, 704 and 706 arranged in a square array unit, for pits. Each of the 16 protrusions such as protrusions 702, 704 and 706, for pits comprise a conical feeder part 708, a flat base part 710, and a connecting shaft part 712 between the feeder part 708 and the flat base part 710. The mould 700 further comprises a punch guide 714 for ease of handling while moulding and de-moulding.

Figure 8:
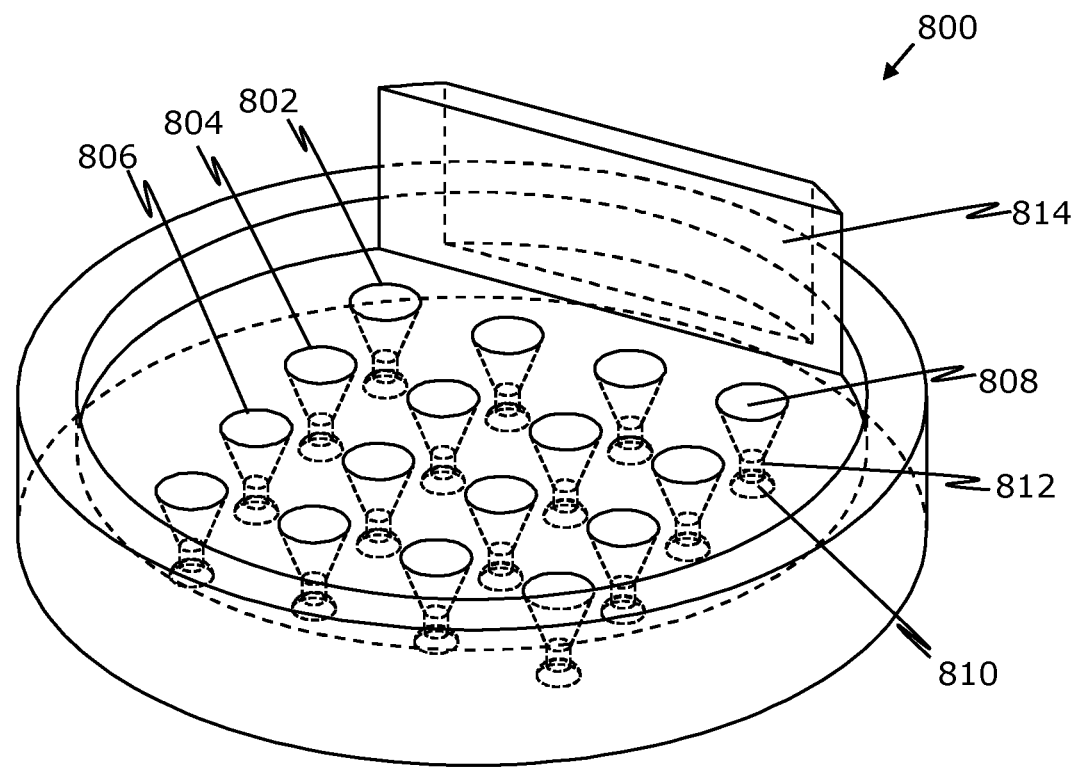
FIG. 8 is a schematic illustration of a pitted reservoir manufactured using the mould of FIG. 7, in accordance with an embodiment of the present disclosure.

Referring to FIG. 8, there is shown an illustration of a pitted reservoir 800, manufactured using the mould 700 of FIG. 7, in accordance with an embodiment of the present disclosure, wherein the pitted reservoir 800 is a negative of the mould 700. The pitted reservoir 800 comprises 16 pits, such as pits 802, 804 and 806, arranged in a square array unit. Each of the 16 pits, such as pits 802, 804 and 806, comprise a feeder part 808, a base part 810, and a shaft part 812 connecting the feeder part 808 and the flat base part 810. The dimensions of the pitted reservoir 800 are defined to fit into a standard 96-well cell culture plate. The pitted reservoir 800 further comprises a punch guide 814 for ease of handling while fitting the pitted reservoir 800 into and out of the standard 96-well cell culture plate. The pitted reservoir 800 is suitable for cultivating a single type of biological sample in each pit 802, 804 and 806. Moreover, two of such pitted reservoirs may be combined with a membrane (not shown) therebetween, to co-culture two or more biological samples in the standard 96-well cell culture plate.

It may be understood by a person skilled in the art that FIG. 7 and FIG. 8 include simplified architectures of the mould 700 and pitted reservoir 800, respectively, for sake of clarity, which should not unduly limit the scope of the claims herein. The person skilled in the art will recognize many variations, alternatives, and modifications of embodiments of the present disclosure.

Figure 9:
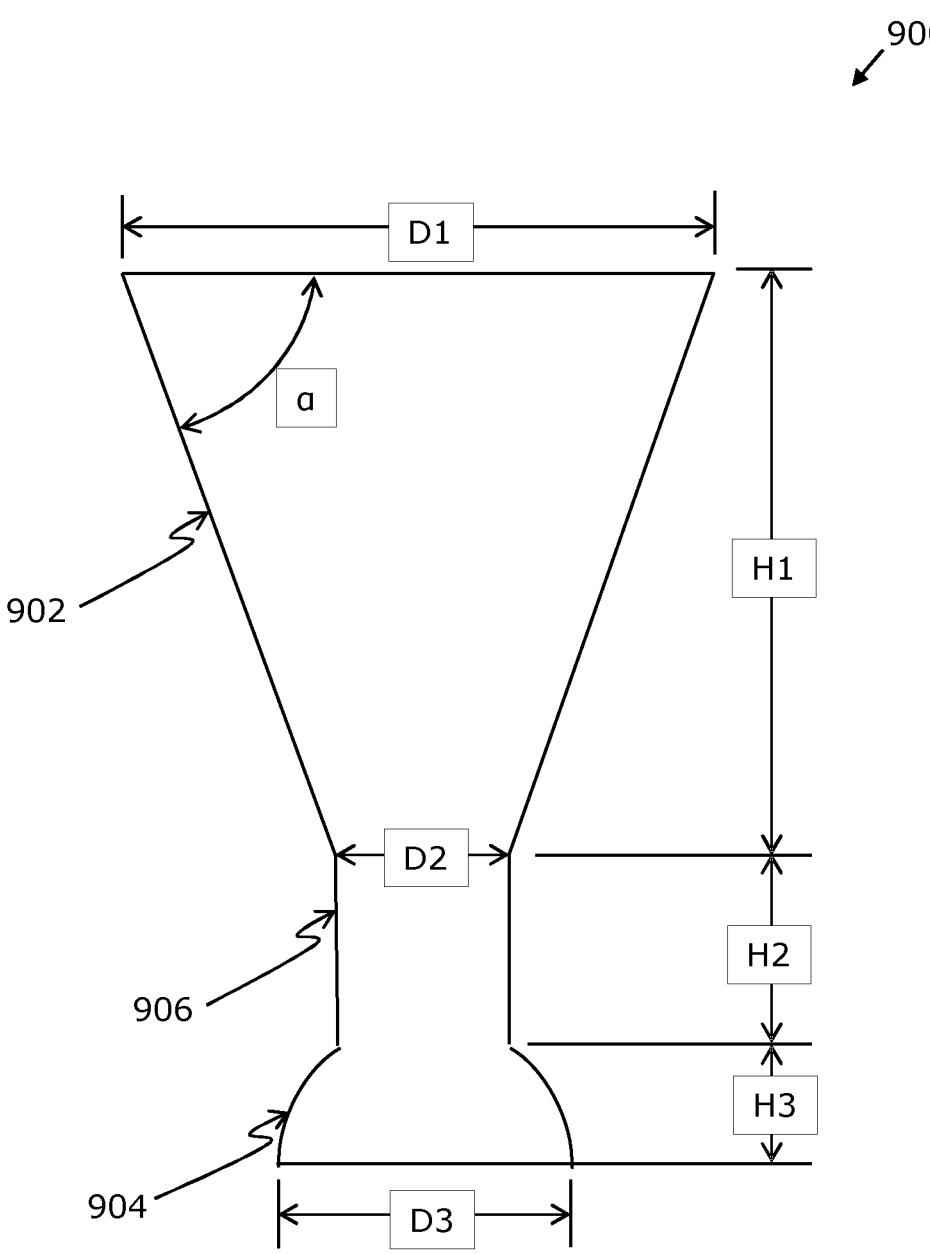
FIG. 9 is a schematic illustration of a pit, in accordance with an exemplary implementation of the present disclosure.

Referring to FIG. 9, there is shown an illustration of a pit 900, in accordance with an exemplary implementation of the present disclosure.

The pit 900 comprises a feeder part 902, a base part 904, and a shaft part 906 connecting the feeder part 902 and the base part 904. As shown, the diameter D1 of the feeder part 902 is 1.0 mm, the diameter D2 of the feeder part 902 is 0.3 mm, the height H1 therebetween is 1.0 mm, the angle α of the feeder part 902 is about 70 degrees, the height H2 of the shaft part is 0.3. Moreover, the diameter D2 of the feeder part coincides with the diameter of the shaft part (not marked), therefore the diameter of the shaft part is 0.3 mm. The diameter D3 of the base part is 0.5 mm and the height H3 of the base part is 0.2 mm.

Referring to FIG. 10, there is shown an illustration of steps of a method 1000 for cell cultivation, in accordance with an embodiment of the present disclosure. At a step 1002, a first biological sample is provided to a base part of two or more pit of a second matrix of pitted reservoirs of a second reservoir structure. At a step 1004, a first predefined amount of culture media is provided to the first biological sample. At a step 1006, the provided first biological sample is incubated for a first incubation time period to produce a first three-dimensional cell culture at a membrane facing the base part of the two or more pits of the second matrix of pitted reservoir. At a step 1008, an orientation of the second reservoir structure is reversed. At a step 1010, a second biological sample is provided to a base part of two or more pits of a first matrix of pitted reservoirs of a first reservoir structure, wherein the first reservoir structure is arranged to be opposite to the second reservoir structure. At a step 1012, a second predefined amount of culture media is provided via an inlet for the culture media to the second biological sample. At a step 1014, the provided second biological sample is incubated for a second incubation time period to produce a second three-dimensional cell culture at the membrane facing the base part of the two or more pits of the first matrix of pitted reservoirs. At a step 1016, one or more analytes is provided to the first matrix of pitted reservoirs.

The steps 1002 and 1016 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An apparatus for cell cultivation, the apparatus comprising:
    a first reservoir structure, the first reservoir structure having a first matrix of pitted reservoirs;
    a second reservoir structure, the second reservoir structure having a second matrix of pitted reservoirs; and
    a membrane,
    wherein the first reservoir structure, the second reservoir structure and the membrane are arranged as a stack,
    wherein the membrane is arranged between the first reservoir structure and the second reservoir structure, and the first matrix of pitted reservoirs is aligned with the second matrix of pitted reservoirs to couple pitted reservoirs of the first matrix of pitted reservoirs together with the pitted reservoirs of the second matrix of pitted reservoirs via the membrane,
    wherein one or more of the pitted reservoirs comprises a common volume and a pit volume, wherein the pit volume comprises of two or more pits, each of the two or more pits comprising:

a feeder part connected to the common volume via a first end of the feeder part, and
a base part connected to a second end of the feeder part via a first end of the base part, and the base part having an opening at a second end of the base part facing the membrane and the base part is configured to accommodate a biological sample for cell cultivation when in use;
wherein the common volume comprises one or more openings for a microfluid channel, and
wherein the base part of the two or more pits has a base volume enclosed by a height ranging between 0.1 to 0.5 millimetres and a diameter ranging between 0.2 to 2.0 millimetres, and wherein a diameter of the base part increases from the second end of the feeder part towards the second end of the base part.

2. The apparatus according to claim 1, wherein the number of pits is four or more and the pits are arranged in the form of an array unit selected from one of: a square array unit or a hexagonal array unit.

3. The apparatus according to claim 1, wherein each of the pitted reservoirs of the first matrix of pitted reservoirs is connected via a respective microfluid channel to a gradient generator, wherein the gradient generator is configured to control a flow rate of one or more analytes to each of the pitted reservoirs of the first reservoir structure.

4. The apparatus according to claim 1, wherein the feeder part of the two or more pits has a feeder volume enclosed by a diameter of the first end ranging between 0.2 to 3.0 millimetres and a diameter of the second end ranging between 0.1 to 1.5 millimetres and a height ranging between 0.1 to 3.0 millimetres forming a conical funnel with an angle (α) ranging between 45 to 80 degrees with respect to a base of the common volume, and wherein the feeder part terminates in the base part of the two or more pits.

5. The apparatus according to claim 1, wherein the two or more pits each have one of: a conical cross-section, a cylindrical cross-section, a spherical cross-section, an elliptical cross-section, or a polygonal shape.

6. The apparatus according to claim 1, wherein the cell cultivation is a three-dimensional cell cultivation.

7. The apparatus according to claim 1, wherein the biological sample is grown into a three-dimensional cell culture on the membrane facing the base part of the two or more pits, and wherein the membrane is a porous membrane with a pore size ranging between 5 to 30 micrometres.

8. The apparatus according to claim 1, wherein the biological sample is selected from any one of: a cell, a tissue, a spheroid, an organoid, a cell line, a monolayer of cultured cells, cells embedded in a matrix, an organ, a microorganism culture or a combination thereof, and wherein a size of the biological sample ranges between 50 to 300 micrometres.

9. The apparatus according to claim 1, wherein the apparatus is manufactured using a fabrication material selected from any of: polydimethylsiloxane (PDMS), biocompatible polymer, thiol-ene polymer, UV-curable epoxy resin-based photoresist, PMMA, polystyrene, PLGA, soft thermoplastic elastomer (sTPE), styrenic block copolymer (BCP), SU-8 polymer, or any combination thereof.

10. The apparatus according to claim 1, wherein the apparatus is used for at least one of: cultivating a single biological sample, co-cultivating of a plurality of biological samples, or analysing the effects of one or more analytes in the cross-gradient flow on the cell cultures of biological samples.

* * * * *